(12) United States Patent
Yu

(10) Patent No.: US 10,012,642 B2
(45) Date of Patent: Jul. 3, 2018

(54) METHODS AND APPARATUS FOR ENHANCED DETECTION OF DISEASES

(71) Applicant: ANPAC BIO-MEDICAL SCIENCE (LISHUI) CO., LTD, Zhejiang (CN)

(72) Inventor: Chris C. Yu, Conneautville, PA (US)

(73) Assignee: ANPAC BIO-MEDICAL SCIENCE (LISHUI) CO., LTD., Zhejiang (CN)

( * ) Notice: Subject to any disclaimer, the term of this patent is extended or adjusted under 35 U.S.C. 154(b) by 19 days.

(21) Appl. No.: 14/776,223

(22) PCT Filed: Mar. 17, 2014

(86) PCT No.: PCT/CN2014/073529
§ 371 (c)(1),
(2) Date: Sep. 14, 2015

(87) PCT Pub. No.: WO2014/139482
PCT Pub. Date: Sep. 18, 2014

(65) Prior Publication Data
US 2016/0282339 A1 Sep. 29, 2016

Related U.S. Application Data

(60) Provisional application No. 61/787,787, filed on Mar. 15, 2013.

(51) Int. Cl.
*G01N 33/50* (2006.01)
*G01N 33/574* (2006.01)

(52) U.S. Cl.
CPC ..... *G01N 33/5091* (2013.01); *G01N 33/5005* (2013.01); *G01N 33/574* (2013.01); *G01N 2800/32* (2013.01)

(58) Field of Classification Search
CPC ..... B01L 2200/0652; B01L 2200/0663; B01L 2300/0645; B01L 3/502761; B01L 2200/0668; B01L 2400/0415; B01L 2400/043; B01L 2400/0487; B01L 3/502707; B01L 2300/0864; B01L 2200/0647; B01L 2300/0627; B01L 2300/06; B01L 2300/0636; B01L 2300/0887; B01L 2300/0681; B01L 2300/00; G01N 33/574; G01N 2800/32; G01N 33/5005; G01N 33/5091
See application file for complete search history.

(56) References Cited

U.S. PATENT DOCUMENTS

| | | | |
|---|---|---|---|
| 6,330,885 B1 | 12/2001 | Weissman et al. | |
| 6,922,118 B2 | 7/2005 | Kubena et al. | |
| 8,828,246 B2 | 9/2014 | Yu | |
| 9,651,542 B2* | 5/2017 | Yu | G01N 35/08 |
| 9,689,863 B2* | 6/2017 | Yu | G01N 33/5091 |
| 2002/0150922 A1* | 10/2002 | Stolk | G01N 33/57419 |
| | | | 435/6.16 |
| 2010/0256518 A1 | 10/2010 | Yu et al. | |
| 2011/0008446 A1 | 1/2011 | Yu et al. | |
| 2014/0079718 A1* | 3/2014 | Thumbikat | A61K 39/395 |
| | | | 424/158.1 |

FOREIGN PATENT DOCUMENTS

| | | |
|---|---|---|
| CN | 102481259 A | 5/2012 |
| CN | 102804333 A | 11/2012 |
| WO | WO-2011/005720 A1 | 1/2011 |
| WO | WO-2011/103041 A1 | 8/2011 |
| WO | WO-2012/003348 A2 | 1/2012 |
| WO | WO-2012/036697 A1 | 3/2012 |
| WO | WO-2012/048040 A2 | 4/2012 |
| WO | WO-2012/128841 A2 | 9/2012 |
| WO | WO-2012/151501 A2 | 11/2012 |
| WO | WO-2013/019930 A2 | 2/2013 |

OTHER PUBLICATIONS

International Search Report dated May 21, 2014 issued in PCT Patent Application No. PCT/CN2014/073529.

* cited by examiner

*Primary Examiner* — Debbie K Ware

(74) *Attorney, Agent, or Firm* — Harness, Dickey and Pierce, P.L.C.

(57) ABSTRACT

The present invention provides methods and apparatus for enhanced detection of a disease by among others enhancing the difference in a microscopic property of diseased cells and normal cells, thereby enhancing the detection sensitivity and specificity.

22 Claims, 15 Drawing Sheets

(a)

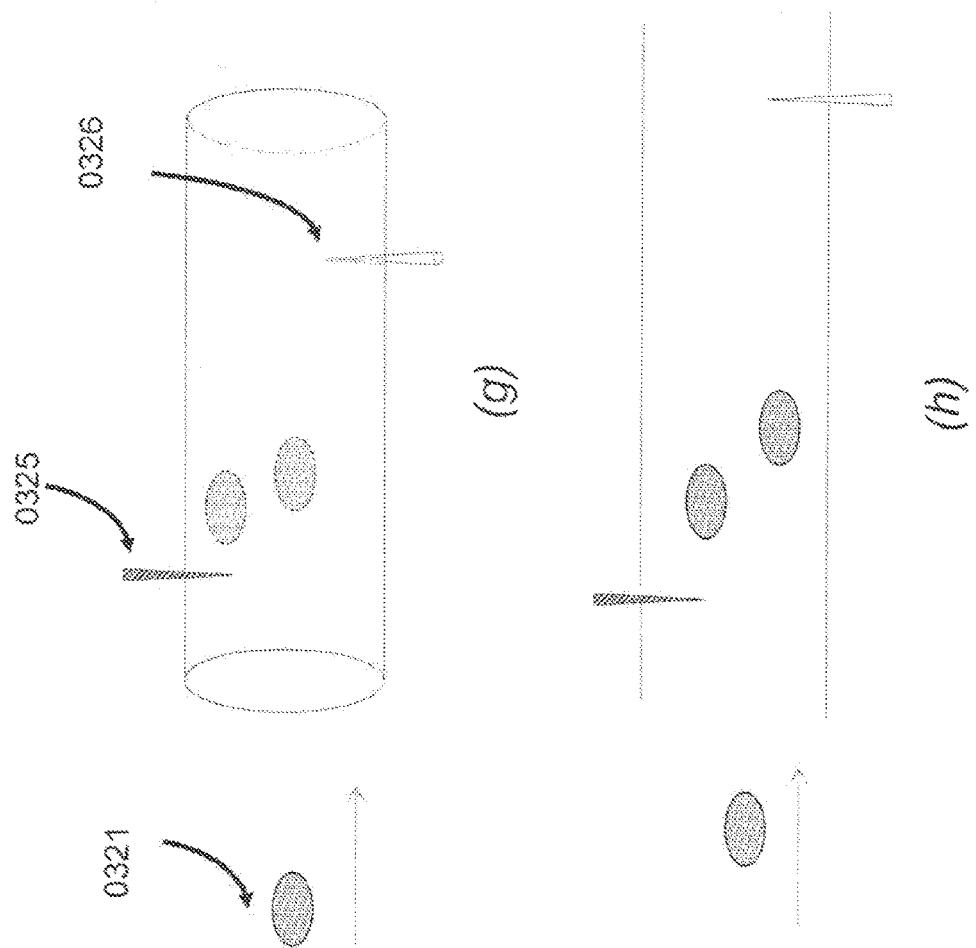

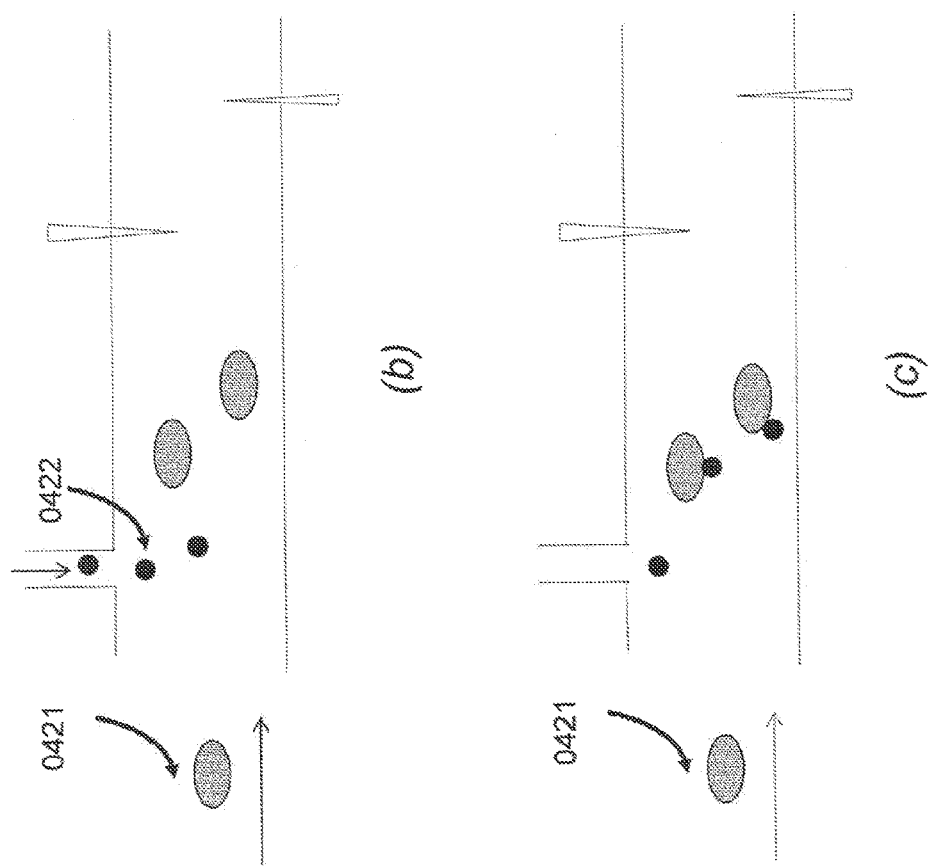

(c)

METHODS AND APPARATUS FOR ENHANCED DETECTION OF DISEASES

CROSS-REFERENCE TO RELATED APPLICATIONS

This application is a national stage application under 35 U.S.C. § 371 of PCT International Application No. PCT/CN2014/073529 which has an International filing date of 17 Mar. 2014, which claims the benefit of U.S. Provisional Application 61/787,787 filed on 15 Mar. 2013. The contents of each application recited above are incorporated herein by reference in their entirety.

BACKGROUND OF THE INVENTION

Diagnosis of a biological sample with low level of expression of a disease such as cancer (whether due to weak detection signal or a very low concentration of diseased components such as circulating tumor cells (CTCs) in cancer screening) is a challenge in modern medicine. Many diseases with low mortality such as cancer and heart diseases have low level of expression (low level of disease components) which makes detection even more difficult. For example, for late stage cancer patients, the level of CTCs in blood stream is as low as one per billion, making detection extremely difficult. As a result, many diseases such as cancer cannot be easily diagnosed at early stage.

Many serious diseases with high morbidity and mortality, including cancer, are very difficult to diagnose early and accurately. Current disease diagnosis technologies typically rely on macroscopic data and information such as body temperature, blood pressure, and scanned images of the body. To detect serious diseases such as cancer and heart diseases, many of the diagnosis apparatus commonly used today are based on imaging technologies, including x-ray, CT scan, and nuclear magnetic resonance (NMR). While they provide various degrees of usefulness in disease diagnosis, most of them cannot provide accurate, totally safe, and cost-effective diagnosis of such serious diseases as cancer at an early stage. Further, many of the existing diagnosis techniques and related apparatus are invasive and sometimes not readily accessible, especially in remote regions or rural areas.

Even the newly emerged technologies such as those deployed in DNA tests have not been proven effective in diagnosing a wide range of diseases in a rapid, reliable, accurate, and cost-effective manner. In recent years, there have been some efforts in using nano technologies for various biological applications, with most of the work focused on gene mapping and moderate developments in the field of disease detection. For instance, Pantel et al. discussed the use of a MicroEelectroMechanical Systems (MEMS) sensor for detecting cancer cells in blood and bone marrow in vitro (see, e.g., Klaus Pantel et al., *Nature Reviews*, 2008, 8, 329); Kubena et al. disclose in U.S. Pat. No. 6,922,118 the deployment of MEMS for detecting biological agents; and Weissman et al. disclose in U.S. Pat. No. 6,330,885 utilizing MEMS sensor for detecting accretion of biological matter.

However, to date, most of the above described technologies have been limited to isolated examples for sensing, using systems of relatively simple constructions and large dimensions but often with limited functions, and lack sensitivities and specificities. Further, some existing technologies utilizing nano-particles and biological approaches have the drawbacks of requiring complicated sample preparation procedures (such as using chemical or biological markers), difficulty in data interpretation, and too much reliance on visual and color change as means of diagnosis (which is subjective and of limited resolution), making them unsuitable for early stage disease detection, e.g., for such serious diseases as cancer, and particularly for routine hospital screening and/or regular physical check-up examinations. Some cannot achieve high degree of sensitivity and specificity simultaneously.

These drawbacks call for novel solutions that not only overcome them but also bring improved accuracy, sensitivity, specificity, efficiency, non-invasiveness, practicality, simplicity, and speed in early-stage disease detection at reduced costs.

The existing detection technology and equipment are dominated by single-technology based single purpose equipment with limited disease detection coverage scope, limited functionalities and low efficiency. They are often very extensive, with large foot print (such as NMR, CT, and x-ray machine). They mainly consist of three large groups: (a) imaging-based technology for mid to late stage cancers, (b) bio-marker based technology which offers some sensitivity to specific type of cancer (but for a given bio-marker, it is typically only sensitive to one type or one sub-type of cancer, with relatively low level of specificity), and (c) genomics based detection technology which is relatively insensitive and long processing time.

Because the images are able to identify the disease only when it is in the mid to late stage, the methods and apparatus that heavily depend on imaging-based technologies are not suitable or capable of detecting early-stage diseases, particularly cancer.

Compared with imaging based technologies, bio-marker can detect certain specific cancer at an earlier stage. However, it is a complicated detection technology and process. With a relatively low specificity, it is prone to false alarm in detection. Further, it is narrow in detection scope and applications in terms of cancer types, since typically for a given bio- marker, it is only sensitive to a particular type or sub-type of cancer. As a result, it may not be suited for a general physical check-up (such as annual physical) for cancer screening. It also may not be used alone for cancer detection and it may require additional diagnosis tools for verifications.

Some other techniques may be capable of detecting certain general parameters of cancer, but they cannot distinguish or identify (i.e., determine) the specific type of cancer. In other words, even if those techniques can alert the existing of a cancerous disease, it cannot specify the type of cancer and hence requires additional diagnosis using other detection technologies. Thus, it alone cannot offer a cancer diagnosis solution.

The existing detection technology has various issues including (a) only capable of detecting mid to late stage cancers (particularly CT, X-ray and NMR technologies), (b) high costs (PET-CT, CT, x-ray and NMR), (c) low detection sensitivity to a number of types of cancers and circulating tumor cells (CTCs), (d) some with low specificity (for example, some bio-marker based technologies), and (e) invasive (such as x-ray and NMR). In particular, there is no viable detection technology for early stage disease screening such as cancer screening which can only detect early stage cancer, but also be able to identify which type of cancer. Because early stage disease screening typically deals with low to very low level of disease expression where disease component has a low to very low concentration, and requires a high level of detection sensitivity and specificity, it is highly desirable to have a novel, efficiency, relatively simple, and cost effective separation method to pre-processing the samples to be detected to enhance the level of disease component (e.g., for cancer detection, to increase the concentration of CTCs in the sample before employing detection techniques) for enhanced detection capabilities (such as sensitivity).

There is a need for providing the ability in terms of both general (cancer detection at an early stage) and specific type(s) of cancer. The limitations described above on the currently existing cancer detection technologies show that no currently existing methods and equipments is able to effectively detect simultaneously both general parameters in a biological entity for detecting of cancer and identifying the specific cancer type.

To overcome the above problems, sometimes, it is necessary to concentrate (enhance) the level of the diseased component in the sample to be measured through separation processes. However, many separation processes and technologies are complicated, expensive, or not effective. So far, there is no viable separation process for wide clinical applications to concentrate a one in a billion cancer disease sample to a level which can be easily detected using existing detection methods. Therefore, there exists a critical importance and great demand to innovate and develop a viable, simple, efficient, and cost effective separation method for concentrating a sample from a patient with a low to very low disease expression (low level of disease component concentration) for enhanced detection capability.

SUMMARY OF THE INVENTION

In general, the present invention provides novel, relatively simple, effective, and inexpensive methods for detecting and identifying a disease (particularly in its early stage) with enhanced sensitivity and specificity.

Particularly, the present invention provides methods for improved detecting a disease in a biological subject, comprising the steps of:
 providing a sample of the biological subject's tissue or organ where the disease may exist, wherein the sample contains potentially diseased cells and normal cell of the biological subject,
 optionally placing the sample in a solvent,
 enhancing the difference in a microscopic property of the potentially diseased cells and normal cells,
 optionally separating the potentially diseased cells and normal cells in the sample,
 optionally increasing the biological expression level or concentration of the potentially diseased cells thus separated; and
 determining the probability of the disease's existence by measuring the biological expression level or concentration of the potentially disease cells and comparing the measurement result with that from a subject free of this disease.

In some embodiments, the methods further include adding an additive to the sample, before the sample is processed for enhanced difference in a microscopic property of the disease cells and normal cells, or during any of the steps in which the sample is processed for detection of the disease.

In some other embodiments, the additive is added to the sample during the step of enhancing the difference in a microscopic property or during the step of separating the diseased cells from the normal cells based on the enhanced difference of a microscopic property.

A suitable additive can be, for instance, an ion, an oxidant, a reductant, an inhibitor, a catalysts, an enzymes, a bio-marker, a chemical-marker, a bio-chemical marker, a bio-active compound, a chemical component, a bio-chemical component, a biological component, an organic component, a metal-organic component, a bio-chemical component, an optical components, a florescence component, a protein, a virus, a coloring agent, an antibody, or a combination thereof.

Examples of a suitable ion include, but are not limited to, $Fe^{3+}$, $Fe^{2+}$, $Ag^+$, $Cu^{2+}$, $Cr^{3+}$, $Na^+$, $K^+$, $Pt^{2+}$, $Mg^{2+}$, $H^+$, $Ca^{2+}$, $Hg^{2+}$, $Al^{3+}$, $NH_4^+$, $H_3O^+$, $Hg_2^{4+}$, $Cl^-$, $F^-$, $Br^-$, $O^{2-}$, $CO_3^{2-}$, $HCO_3^-$, $OH^-$, $NO_3^-$, $PO_4^{3-}$, $SO_4^{2-}$, $CH_3COO^-$, $HCOO^-$, $C_2O_4^{2-}$, and $CN^-$.

Examples of a suitable oxidant include, but are not limited to, oxygen, ozone, hydrogen peroxide, an inorganic peroxide, nitric acid, a nitrate compound, a chromium compound, a permanganate compound, sulfuric acid, persulfuric acid, fluorine, chlorine, bromine, iodine, chlorite, chlorate, perchlorate, a halogen compound, hyperchlorite, a hypohalite compounds, sodium perborate, nitrous oxide, sliver oxide, osmium tetroxide, Tollens' reagent, 2,2'-dipyridyldisulfide, urea, silver nitrate, ferric nitrate, urea nitrogen, blood urea nitrogen, potassium permanganate, and any combination thereof.

Examples of a suitable halogen compound include, but are not limited to, 4-chlorotoluene, dibromopentane, bromoethane, 2-chloropropane, fluorocyclopentane, or 2-iodo-2-methylpentane; the hypohalite compound is hypoiodous acid, hypobromite, hypochlorite, and hypofluorous acid.

Examples of a suitable reductant include, but are not limited to, nascent hydrogen, a compound containing $Fe^{2+}$ ion (e.g., iron(II) sulfate), sodium amalgam, sodium borohydride, a sulfite compound, hydrazine, a compound containing the $Sn^{2+}$ ion, zinc-mercury amalgam, lithium aluminum hydride, Lindlar catalyst, formic acid, oxalic acid, ascorbic acid, a phosphite, a hypophosphite, phosphorous acid, or a combination thereof.

Example of a suitable bio-active compound include, but are not limited to, glucose, fructose, pyruvate, galactose, amino acid, acetic acid, glyoxylic acid, oxalic acid, propionic acid, acetic acid, or an enzyme.

Examples of a suitable enzyme include, but are not limited to, an oxidoreductase (e.g., dehydrogenase, luciferase, or DMSO reductase), transferase, hydrolase, lyase, isomerase, ligase, RNA-enzyme, DNA polymerase, RNA polymerase, hexokinase (e.g., pyruvate carboxylase or PEP carboxylinase), aminoacyl tRNA synthetase, ribosome, an artificial enzyme, or a cofactor-bound thereof.

In yet some other embodiments of the methods, a first additive is added to the sample before the sample is handled for enhanced difference in a microscopic property of disease cells and normal cells, and a second additive is added during any of the steps in which the sample is handled for detected of the disease. The first and second additives can be the same or different.

In yet still some other embodiments, the step of separating the diseased cells and normal cells in the sample includes subjecting the sample to one or more filters.

In some examples, the one or more filters differentiate the diseased cells and normal cells by their electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical property, or a combination thereof.

Examples of the microscopic property include, but are not limited to, an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical property, and any combination thereof.

Examples of the electrical property include, but arc not limited to, surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; examples of the optical property include, but are not limited to, optical absorption, optical transmission, optical reflection, optical-electrical property, brightness, or fluorescent emission; examples of the chemical property include, but are not limited to, pH value, chemical reaction, bio-chemical reaction, bio-electro-chemical reaction, reaction speed, reaction energy, speed of reaction, oxygen concentration, oxygen consumption rate, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; examples of the physical property include, but are not limited to, density, shape, volume, or surface area; examples of the biological property include, but are not limited to, surface shape, surface area, surface charge, surface biological property, surface chemical property, pH, electrolyte, ionic strength, resistivity, cell concentration, property relating to bio-markers, or biological, electrical, physical or chemical property of solution; examples of the acoustic property include, but are not limited to, frequency, speed of acoustic waves, acoustic frequency and intensity spectrum distribution, acoustic intensity, acoustical absorption, or acoustical resonance; examples of the mechanical property include, but are not limited to, internal pressure, hardness, flow rate, viscosity, shear strength, elongation strength, fracture stress, adhesion, mechanical resonance frequency, elasticity, plasticity, or compressibility.

In some embodiments, the methods further include applying an external force or energy to the sample before the sample is processed for enhanced difference in a microscopic property of the disease cells and normal cells, or during any of the steps in which the sample is handled for detected of the disease, and the application of the external force or energy results in enhanced difference of a microscopic property of diseased cells and normal cells.

Examples of a suitable external force or energy include, but are not limited to, a physical, chemical, biological, mechanical, thermal, optical, acoustical, electrical, magnetic, electromagnetic, electro-mechanical, electro-chemical, electro-chemical-mechanical, bio-chemical, bio-mechanical, bio-optical, bio-physical, bio-electro-mechanical, bio-electro-chemical, or bio-electro-chemical-mechanical, electro-optical, electro-chemical optical force or energy.

Examples of the microscopic property include, but are not limited to, an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro thermal-optical, bio-electro-chemical-mechanical, physical or mechanical property, or a combination thereof.

In some embodiments, the electrical property is surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, speed of reaction, oxygen concentration, oxygen consumption rate, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, property relating to bio-markers, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, shear strength, elongation strength, fracture stress, adhesion, mechanical resonance frequency, elasticity, plasticity, or compressibility.

In some embodiments, the methods of this invention not only detects the existence of disease in the biological subject by differentiating normal biological material from diseased biological material, but also obtain information on the type or types of the disease thereby differentiating the different types of disease.

Examples of the disease that can be detected by a method of this invention, with enhanced sensitivity and selectivity, include but are not limited to cancer and heart disease. For instance, the cancer can be bladder cancer, breast cancer, colon cancer, rectal cancer, endometrial cancer, kidney cancer, leukemia cancer, lung cancer (including bronchus), melanoma cancer, non-Hodgkin lymphoma, pancreatic cancer, prostate cancer, or thyroid cancer.

In some examples, the differentiation of different types of disease is based in part on the geometry of the detection unit or the biological sample; or the differentiation of different types of disease is based in part on the geometry of the detection unit, probing signal, change in the probing signal, or the biological sample. Alternatively, the differentiation of different types of disease can be based in part on the geometry of the detection unit, probing signal, change in the probing signal and the biological sample.

In some embodiments, the differentiation of different types of disease is based in part on the cell surface properties, cell membrane properties, oxygen level, oxygen location, oxygen bonding, electric charge density, electric charge location, or dynamic properties of the electric charge of the biological sample. Examples of the cell surface or cell membrane properties include, but are not limited to, surface absorption and adsorption ability of the biological sample, the oxygen level, oxygen bonding on the cell surface or membrane, ion concentration, ion gradient, membrane resting potential, cell surface charge, the permeability and transportation ability of the membrane.

The present invention in general relates to a class of innovative and integrated micro-devices for carrying out much enhanced disease detection and identification at microscopic levels, in vivo or in vitro, on a single cell, a single biological molecule (e.g., DNA, RNA, or protein), a single biological subject (e.g., a single virus), or other sufficiently small unit or fundamental biological composition. This class of micro-devices can be made by using state-of-the-art micro-device fabrication technologies and novel process flows such as integrated circuit fabrication technologies. As used herein, the term "disease detection micro-device" can be interchanged with such terms as disease detection device or apparatus integrated with micro-devices, or any other similar terms of the same meaning. The micro-devices of this invention contain multiple micro units to perform different functions and optionally detect multiple parameters of a biological subject to be detected or analyzed. Optional components of the apparatus includes means to perform at least the function of addressing, controlling, forcing, receiving, amplifying, manipulating, processing, analyzing, making decisions (e.g., logic decisions), or storing information from each probe. Such means can be, e.g., a central control unit that includes a controlling circuitry, an addressing unit, an amplifier circuitry, a logic processing circuitry, an analog device, a memory unit, an application specific chip, a signal transmitter, a signal receiver, or a sensor.

These disease detection micro-devices are capable of detecting diseases at their early stages with a higher and much improved degree of sensitivity, specificity, speed, simplicity, practicality, convenience (e.g., simpler operating procedures or reduced apparatus size), or affordability (e.g., reduced costs), with substantially reduced to no invasiveness and side effects. Accordingly, the micro-devices of this invention are capable of perform at a much higher level than those of conventional disease detection apparatus or technologies.

The methods of this invention can be practiced by micro-devices described in the following patent applications: U.S. 61/672,231, U.S. 61/749,661, PCT/US2011/054979, PCT/US2012/022921, PCT/US2012/036551, PCT/US2012/049287, PCT/US 2011/042637, PCT/US2011/024672, U.S. 61/608,363, the contents of all of which are incorporated herein by their entireties.

Accordingly, the present invention also provides an apparatus for detecting a disease in a biological subject. The apparatus includes a system for delivering the biological subject to be detected, a device for injecting an additive which interacts with the biological subject, and a probing and detecting device for probing and detecting the biological subject, wherein the biological subject contains normal cells and potentially diseased cells, the normal cells and potentially diseased cells differ in the level of at least one microscopic property, and the addictive interacts with the biological subject to enhance the difference in the at least one microscopic property. Examples of suitable additive include an ion, an oxidant, a reductant, an inhibitor, a catalysts, an enzymes, a bio-marker, a chemical-marker, a bio-chemical marker, a bio-active compound, a chemical component, a bio-chemical component, a biological component, an organic component, a metal-organic component, a bio-chemical component, an optical components, a florescence component, a protein, a virus, a coloring agent, an antibody, or a combination thereof.

Examples of fabrication techniques or processes that can be used to make the micro-devices for the methods of this invention include, but are not limited to, mechanical, chemical, physical-chemical, chemical mechanical, electrical, physical, bio-chemical, bio-physical, bio-physical mechanical, electro-mechanical, bio-electro-mechanical, micro-electro-mechanical, electro-chemical-mechanical, electro-bio-chemical-mechanical, nano-fabrication techniques, integrated circuit and semiconductor manufacturing techniques and processes. For a general description of some of the applicable fabrication technologies, see, e.g., R. Zaouk et al., *Introduction to Microfabrication Techniques*, in Microfluidic Techniques (S. Minteer, ed.), 2006, Humana Press; *Microsystem Engineering of Lab-on-a-chip Devices,* 1st Ed. (Geschke, Klank & Telleman, eds.), John Wiley & Sons, 2004. Micro-device functionalities would at least include sensing, detecting, measuring, diagnosing, monitoring, and analyzing for disease diagnosis. Multiple micro-devices can be integrated onto a piece of detection apparatus to make the apparatus more advanced and sophisticated for further enhanced measurement sensitivity, specificity, speed and functionalities, with ability to measure the same parameter or a set of different parameters.

As used herein, the term "additive" includes an ion, an oxidizer or oxidant, a reducing agent, an inhibitor, a catalyst, an enzyme, a bio-marker, a chemical-marker, a bio-chemical marker, a chemical component, a bio-chemical component, a biological component, an organic component, a metal-organic component, a bio-chemical component, an optical component, a florescence component, a protein, a virus, a coloring agent, an antibody, or a combination thereof.

As used herein, the term "or" is meant to include both "and" and "or." In other words, the term "or" may also be replaced with "and/or."

In some embodiments, the biological sample is a DNA, telomere of DNA, RNA, chromosome, cell, cell substructure, protein, tissue, virus, blood, urine, sweat, tear, saliva, or organ tissue.

In some embodiments, the liquid solution is an aqueous solution or a solution in an organic solvent.

In some embodiments, the disease is a cancer.

In some embodiments, the cancer is bladder cancer, breast cancer, colon cancer, rectal cancer, endometrial cancer, kidney cancer, leukemia cancer, lung cancer (including bronchus), melanoma cancer, non-Hodgkin lymphoma, pancreatic cancer, prostate cancer, or thyroid cancer.

In some embodiments, the additive exists as a liquid solution, solid nanoparticles, or gas.

In some embodiments, the liquid solution is an aqueous solution or an organic solution and comprises potassium permanganate, glucose or a glucose compound, hydrogen phosphate, pyruvate acid, sodium pyruvate, bromide pyruvate, bromopyruvic acid, acetic acid, propionaldchyde, glyccrldchydc, methylglyoxal, lactate dehydrogenase, alanine, lactic acid, amino acid, a protein, calcium, potassium, sulfur, sodium, magnesium, copper, zinc, selenium, molybdenum, fluorine, chlorine, iodine, manganese, cobalt, iron, or an enzyme. Examples of a suitable enzyme include a hexokinase (e.g., pyruvate carboxylase and PEP carboxylinase), oxidoreductases (dehydrogenase, luciferase, DMSO reductase), transferases, hydrolases, lyases, isomerases, ligases, RNA-enzyme, DNA polymerase, RNA polymerase, aminoacyl tRNA synthetases, and ribosomes, artificial enzyme (for example, scaffolded histidine residues), and enzymes with their respective cofactors.

In some embodiments, the gas and liquid solution comprises $O_2$, $O_3$, CO, $CO_2$, calcium, sodium, potassium, sulfur, sodium, magnesium, copper, zinc, selenium, molybdenum, fluorine, chlorine, iodine, manganese, cobalt, iron, or carbon based organic groups including but not limited to organometallic compound group, aldehyde (carbonyl group), ketone (carbonyl group), carboxylic acid (carboxyl group), amine (amino group), amino acid (amino group plus carboxyl group) and alcohol (hydroxyl group).

In some embodiments, a method of this invention further includes mixing the biological sample to be tested with an additive before the detection to enhance the sensitivity and/or specificity of the detection.

In some embodiments, a method of this invention further includes mixing the biological sample to be tested with an additive during the detection to enhance the sensitivity and/or specificity of the detection, during which the dynamic information in interaction between the biological subject to be tested and the additive is obtained.

Still in some other embodiments, a method of this invention further includes mixing the biological sample to be tested with at least two additives, either together or separately, before or during the detection or both.

In some embodiments, the additive comprises a chemical additive, a bio-chemical additive, a biological additive, a solid particle, or a nano-particle with a high surface area.

In some embodiments, mixing of the biological material to be tested with the additive results in one or multiple reactions between the biological subject to be tested and the additive, or among the biological subject to be tested, other component(s) in the liquid solution, and the additive. The reaction may include an oxidation, reduction, catalytic, chemical, biological, bio-chemical, bio-physical, bio-mechanical, bio-optical, bio-electrical, electro-optical, bio-thermal, bio-electro-optical, bio-electro-mechanical, exothermic, or chain reaction.

In some instances, the reaction is or causes a chain reaction in which a signal (particularly a weak signal) to be detected can be amplified, thereby enhancing the detection sensitivity and specificity, e.g., for disease such as one or more types of cancer, or for differentiating different types of disease.

In some other instances, the reaction will enhance the sensitivity of detecting oxygen level in the biological sample to be tested.

In the methods of this invention, at least two additives can be added to the biological sample to be detected at the same time or different times (with different or same time interval).

As a first example, they can be added in the following sequence: adding an oxidizer to the liquid solution containing the biological subject to be tested first; optionally adding an catalyst; optionally adding a bio-chemical additive; optionally adding an inhibitor; optionally adding a bio-marker; optionally adding a chemical; optionally adding an enzyme; and optionally adding a reducing agent.

As a second example, the additives are added in the following sequence: adding a catalyst to the liquid solution containing the biological subject to be tested first; optionally adding an oxidizer; optionally adding a bio-chemical additive; optionally adding an inhibitor; optionally adding a bio-marker; optionally adding a chemical; optionally adding an enzyme; and optionally adding a reducing agent.

As a third example, the additives are added in the following sequence: adding a bio-chemical additive to the liquid solution containing the biological subject to be tested first; optionally adding an catalyst; optionally adding a reducing agent; optionally adding an inhibitor; optionally adding a bio-marker; optionally adding a chemical; optionally adding an enzyme; and optionally adding an oxidizer.

As a fourth example, the additives are added in the following sequence: adding a reducing agent to the liquid solution containing the biological subject to be tested first; optionally adding an catalyst; optionally adding a bio-chemical additive; optionally adding an inhibitor; optionally adding a bio-marker; optionally adding a chemical; optionally adding an enzyme; and optionally adding an oxidizer.

As a fifth example, the additives are added in the following sequence: adding to a nano-particle dispersion an additive selected from a group comprising of an oxidizer, a reducing agent, an inhibitor, a catalyst, an enzyme, a protein, a virus, a coloring agent, a bio-marker, a chemical-marker, an organic compound, a metal-organic compound, an antibody, a bio-chemical-marker, chemical, bio-chemical, a biological component, a thermal material, and an optical material including fluoresce materials; mixing the above dispersion well; optionally processing the above dispersion at a desired temperature for a desired time; and adding the above dispersion to a liquid phase solution containing a biological subject to be tested.

As a sixth example, the additives are added in the following sequence: adding to a nano-particle dispersion an additive selected from a group comprising of an oxidant, a reductant, an inhibitor, a catalyst, an enzyme, a protein, a virus, a coloring agent, a bio-marker, a chemical-marker, an organic compound, a metal-organic compound, an antibody, a bio-chemical-marker, a chemical, a bio-chemical, a biological component, a thermal material, and an optical material including fluoresce materials; mixing the above dispersion well; optionally processing the above dispersion at a desired temperature for a desired time; and adding a liquid phase solution containing a biological subject to be tested to the above dispersion.

In some embodiments of the methods of this invention, the additive can include an oxidizer, a reducing agent, an inhibitor, a catalyst, an enzyme, a protein, a virus, a coloring agent, a bio-marker, a chemical-marker, an organic compound, a metal-organic compound, an antibody, a bio-chemical-marker, chemical, bio-chemical, a biological component, a thermal material, and an optical material including fluoresce materials. Examples of the catalyst include an enzyme, an ion, a biological component, a chemical component which speeds up reactions, or a combination thereof.

In some other embodiments, the additives are pre-added to the biological samples to be tested before being introduced into a micro-device for detection.

In some other embodiments, the additives are added to the micro-device through separate inlet and mixed with the biological samples to be tested in the micro-device before detection.

In yet some other embodiments, the additives are added to the micro-device through separate inlets and mixed with the biological samples to be tested in the micro-device during detection.

In some embodiments, a property of the biological sample is measured at the microscopic level using the micro-device after the biological sample is mixed with the additive or additives. The property to be measured can include an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical property, or a combination thereof.

The methods of this invention not only allows detection of the existence of disease in the biological subject by differentiating normal biological material from diseased biological material, but also obtaining information on the type or types of the disease thereby differentiating the different types of disease (e.g., cancer). The differentiation of different types of disease can be based in part on the geometry of the detection unit, probing signal, change in the probing signal, and/or the biological sample; or on the cell surface properties, cell membrane properties, oxygen level, oxygen location, oxygen bonding, electric charge density, electric charge location, or dynamic properties of the biological sample. Examples of the cell surface or cell membrane properties include surface absorption and adsorption ability of the biological sample, the oxygen level, oxygen location, oxygen bonding on the cell surface or membrane, ion concentration, ion gradient, membrane resting potential, cell surface charge, or the permeability and transportation ability of the membrane. The above-stated properties can be static or dynamic and changing.

In some embodiments, the additives include an oxidizer, an enzyme, a reducing agent, an inhibitor, a bio-marker, a bio-chemical component, a chemical component, a biological component, a protein, a virus, a thermal component, an optical component, a fluoresce material, or a catalyst, which are added to the biological at different times before the detection.

In some embodiments, the additives include at least a bio-active compound (e.g., a protein that binds the biological material).

In some embodiments, at least two additives are mixed before they are added to the biological sample to be detected.

In some embodiments, the complex of the biological sample and additives is separated before being detected by the detection unit.

The methods of this invention can result in a higher degree of sensitivity for and specificity of the disease to be detected than a method without the application of the additive.

BRIEF DESCRIPTIONS OF THE FIGURES

DETAILED DESCRIPTION OF THE INVENTION

In one aspect, the present invention provides micro-devices for detecting at the microscopic level a property of a biological material contained in a liquid or existing in a liquid state, comprising, an inlet for the biological material to enter the micro-device, an optional pre-treatment unit, a probing unit, a detection unit, a system controller, and an exit for the residual biological material or waste to he ousted from the micro-device.

The probing unit and the detection unit each can be fabricated by methods previously developed by the same inventors and described in earlier applications. See, e.g., WO 2011/103041 and WO 2011/005720, the contents of which arc incorporated herein by reference in their entireties.

Figure 1:
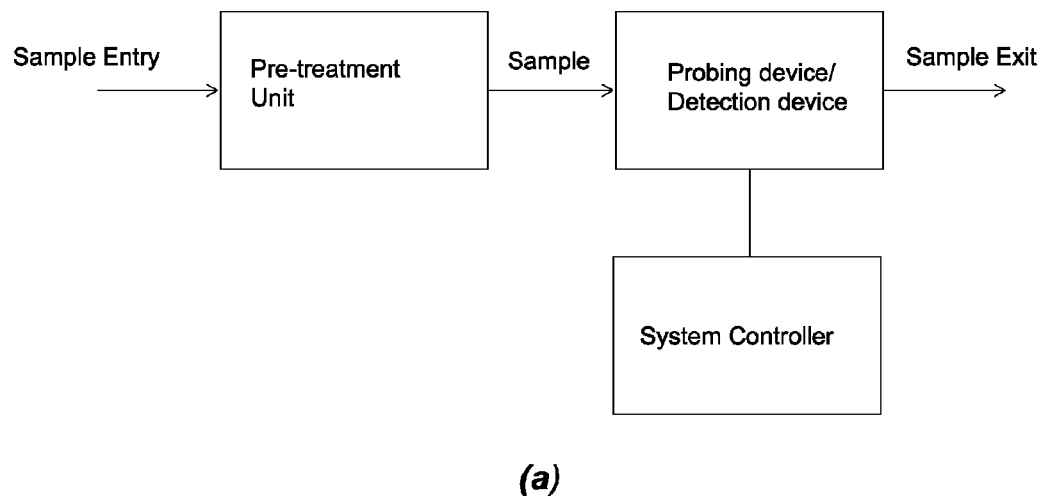
FIG. 1 shows the diagram of an apparatus of this invention for detecting disease, and a system controller contained in the apparatus.
Figure 1:
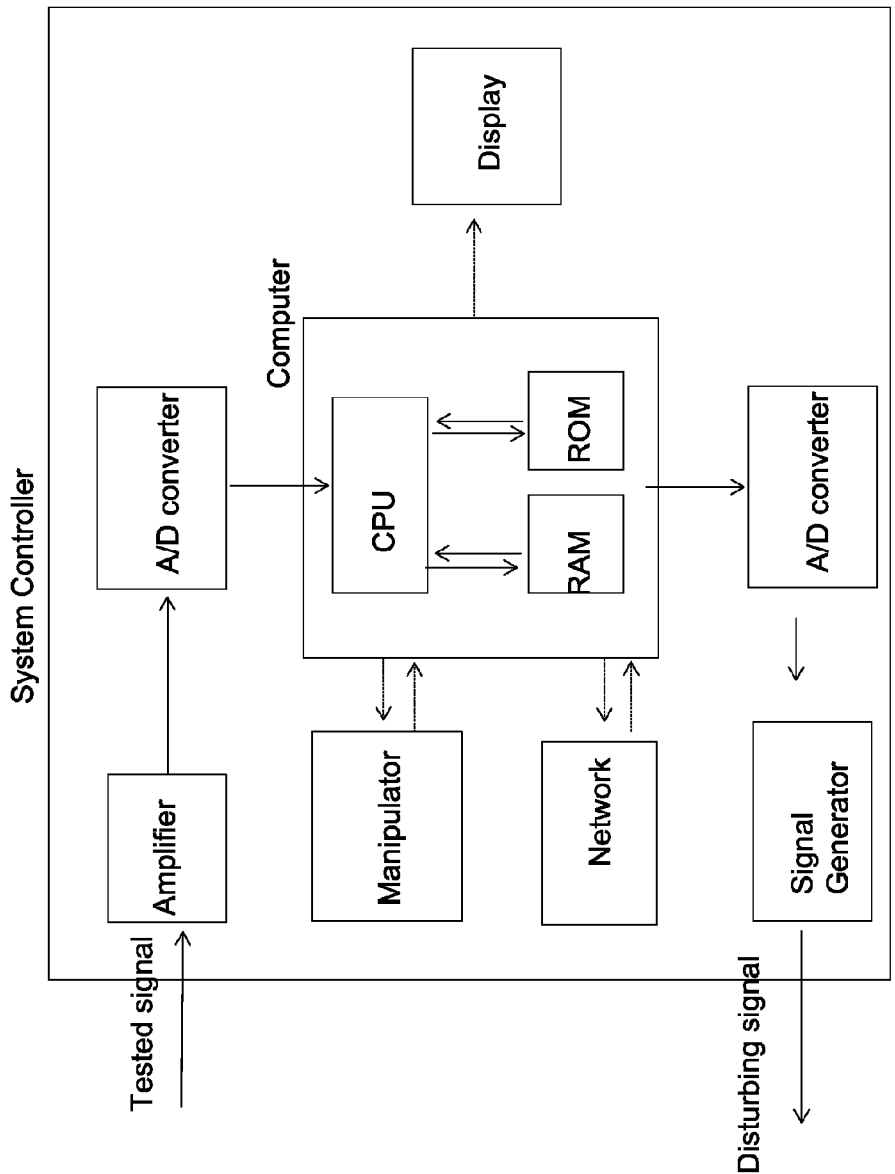

FIG. 1 shows an example of the micro-devices of this invention for detecting at the microscopic level a property of a liquid or dissolved solution (e.g., food, beverage, oil, chemical, drug, blood, urine, sweat, saliva, and other biological liquid). FIG. 1(a) illustrates a micro-device with at least a sample entry, a sample exit, a pre-treat unit, a probing device, a detection device, and a system controller. FIG. 1(b) illustrates a system controller's diagram. In the system, the tested signal is collected by the system controller through amplifier and converter. It is then processed and analyzed by the computer. The analyzed result is transmitted to a recorder or displayed on a display device. The disturbing (probing) signal is initiated by operator through manipulator. It is then processed by the computer, convertor, and then produced by the signal generator, then being applied to the objects to be measured.

In one embodiment, the micro-devices comprise a biological sample pre-treatment unit in which diseased biological items (such as circulating tumor cells) are concentrated, an inlet for bringing in an additive, single channels in which biological sample can flow through, multiple channels in which biological sample can flow through, a detection probe unit for sending disturbing signals, a detection detector unit for sensing response signals, or an outlet for biological sample to flow out. The sample pre-treatment unit has one stage or multiple stages (which comprise filtration, electrophoresis, bio-marking, centrifuge, or optical processing) for concentrating diseased items. The detection detector unit comprises at least one high sensitivity detector integrated onto the walls of the channels for signal detection.

Figure 2:
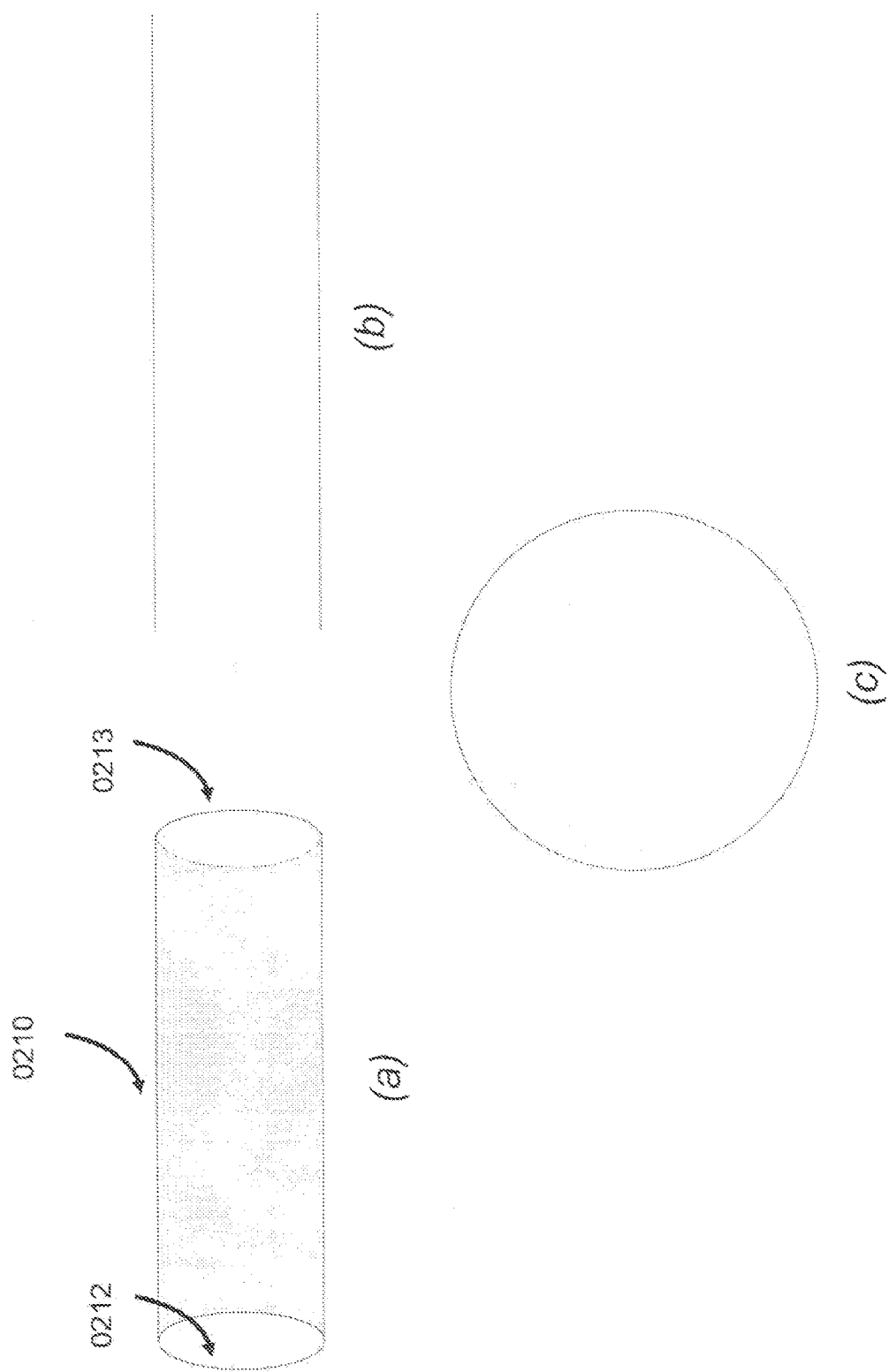
FIG. 2 illustrates an example of capillary tube which can be included in an apparatus of this invention.
Figure 2:
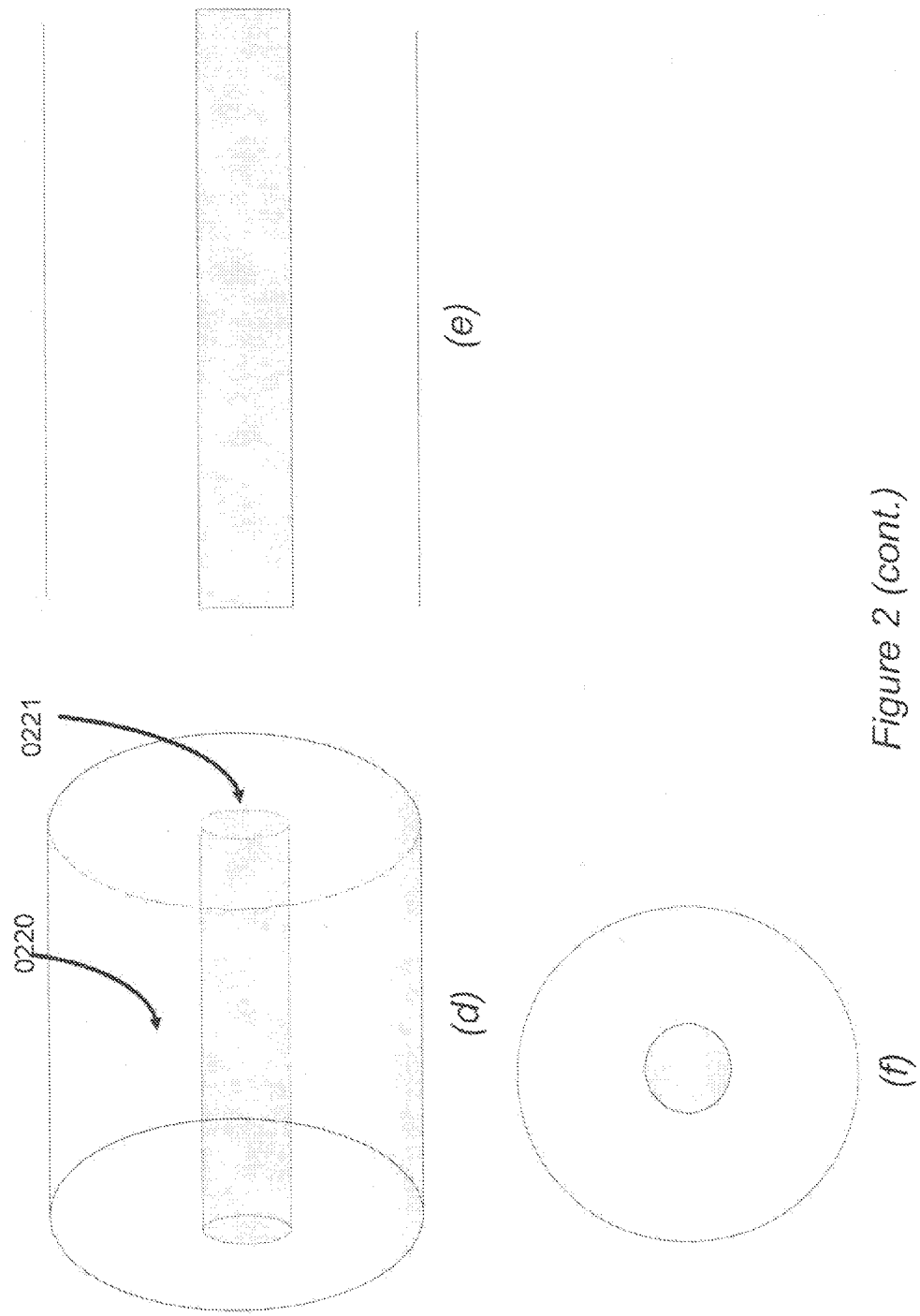

Each micro-device of this invention can further include a capillary tube having two terminal openings and a sidewall with an interior surface and an outer surface, wherein one of the two terminal openings is the inlet of the micro-device and the other terminal opening is the outlet of the micro-device. As illustrated in FIG. 2 (a), 0210 is a capillary tube with at least one inlet (0212) and at least one outlet (0213). FIG. 2 (b) is a perspective view of the capillary tube. FIG. 2 (c) is a cross-sectional view of the tube. The cross-section can be a circular, elliptical, square, rectangular, tri-angular, or polygon shape. As illustrated in FIG. 2 (d), 0220 is a capillary tube with a core 0221, and a channel is defined between the outer sidewall and the core. FIG. 2 (*e*) is a perspective view of the capillary tube, and FIG. 2 (*f*) is the vertical (cross-sectional) view.

Figure 3:
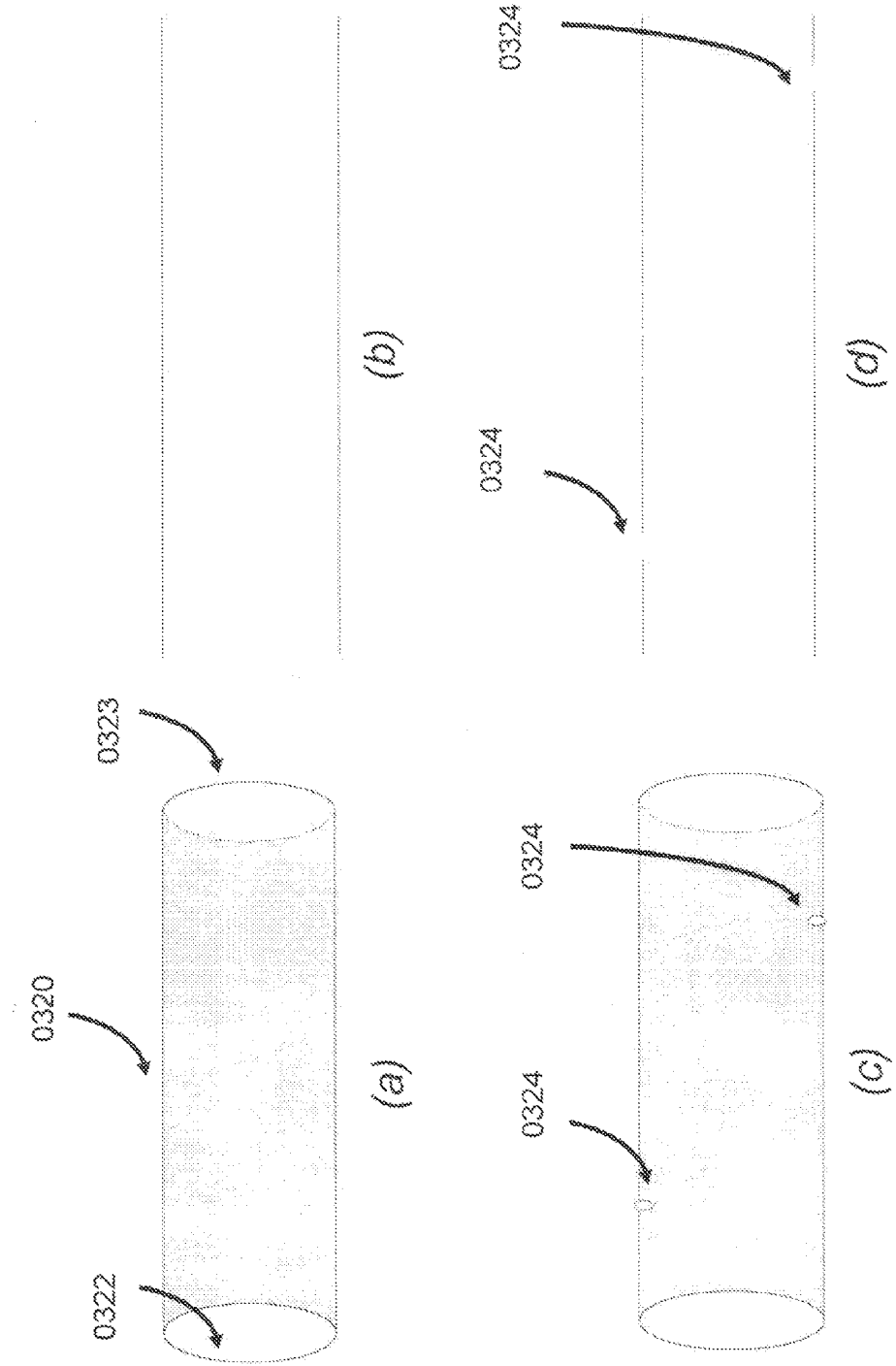
FIG. 3 illustrates another example of capillary tube, with optional probing and detection units, which can be included in an apparatus of this invention.
Figure 3:
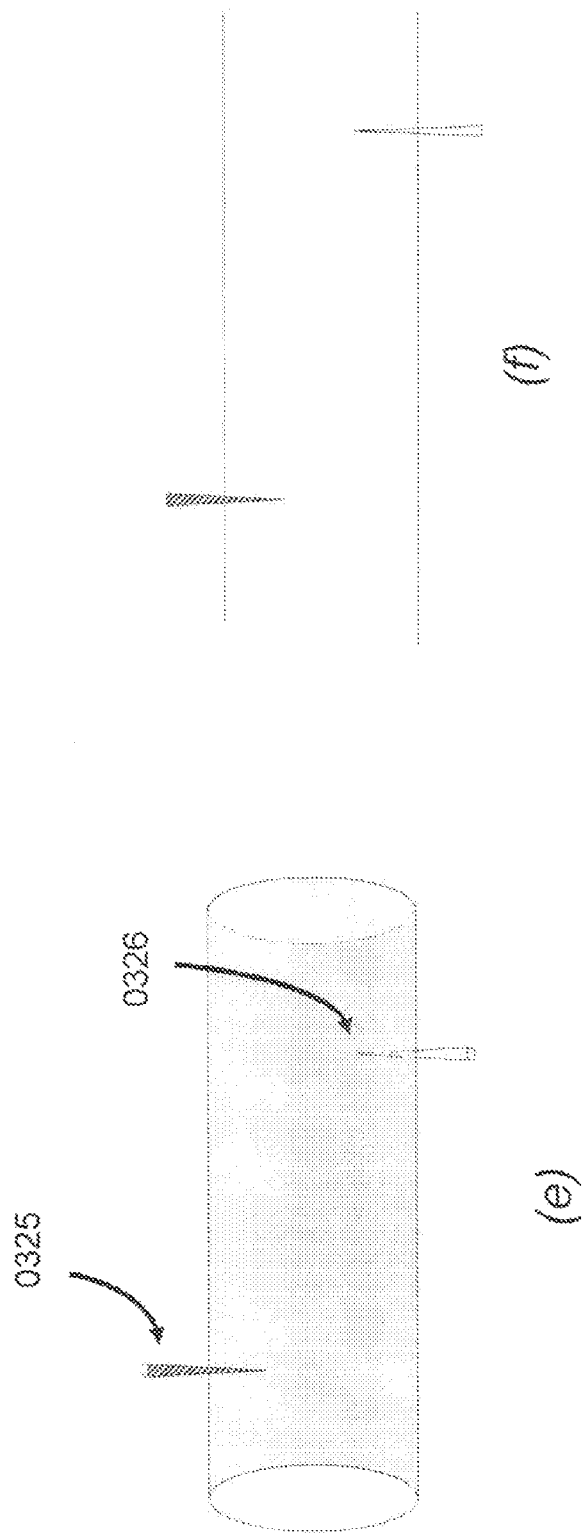
Figure 3:
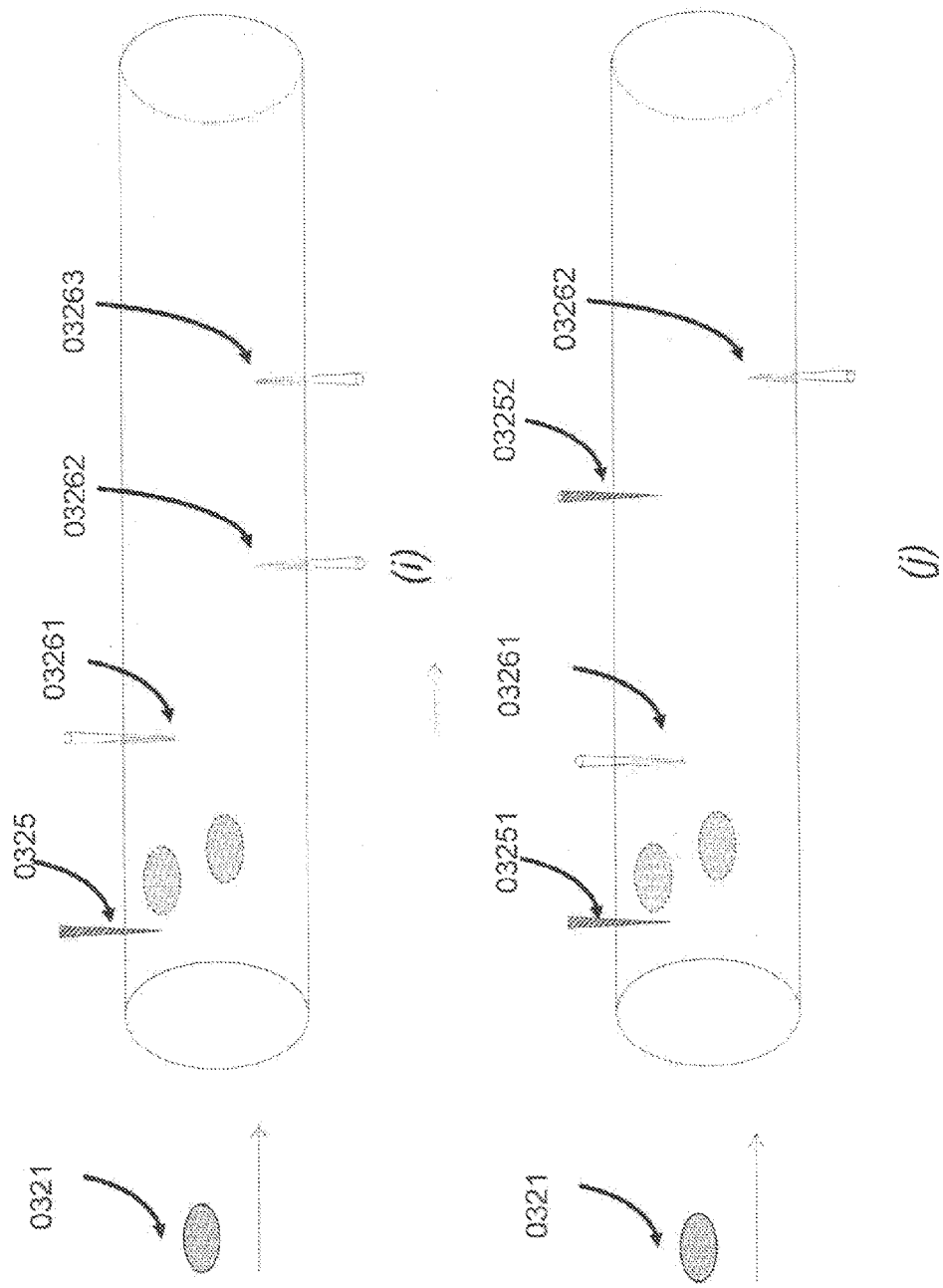

The capillary tube comprises one or more pin-holes each of which runs through the exterior and interior surfaces of the capillary tube's sidewall and houses a probing unit or a detecting unit. As illustrated in FIG. 3(*a*), 0320 is a capillary tube with at least one inlet (0322) and at least one outlet (0323). FIG. 3(*b*) is a perspective view of the capillary tube. As illustrated in FIG. 3(*c*), 0324 is a pin-hole which penetrates the sidewall of the capillary tube 0320. FIG. 3 (*d*) is a perspective view. The pin-holes can be fabricated by a mechanical, electric, magnetic, electro-magnetic, radio-active, ionic, thermal, optical, acoustical, chemical, electro-mechanical, electro-chemical, electro-chemical-mechanical method, or combination thereof.

The capillary tube can optionally be transparent. The preferred transparent materials to fabricate the capillary tube include glass, $SiO_2$ and organic polymeric materials. The inner diameter of the capillary tube ranges, e.g., from about 10 um to about 10 mm As illustrated in FIG. 3(*e*), a probing unit (0325) and a detecting unit (0326) are assembled penetrating the sidewall of the capillary tube. The probing unit and detecting unit are capable of sending probing signal and detecting at the microscopic level an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical property of the biological subject. The probing unit is also capable of generating an electric, magnetic, electro-magnetic, radio-active, ionic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical signal.

FIG. 3(*g*) illustrates an embodiment of examining tube and FIG. 3(*h*) is its perspective view. When the sample to be tested passes through the tube, the disturbing unit 0325 releases a pulse or disturbing signal which stimulates the sample, and then the related parameters is then probed and collected by sensor 0326. The disturbing pulse comprises an electric, magnetic, electro-magnetic, radio-active, ionic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical signal, or a combination thereof. The probing sensor collects an electric, magnetic, electro-magnetic, radio-active, ionic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical or mechanical signal, or a combination thereof.

FIGS. 3(*i*) and 3(*j*) illustrate additional embodiments in which more than one probing unit or/and more than one detecting unit (e.g., 0325, 03261, 03262, 03263; 03251, 03261, 03252, 03262) are included in the capillary tube.

Although a capillary tube is particularly exemplified herein, micro-devices containing other shapes of channels are also applicable to this invention. Such micro-devices have been previously described else by the inventors. See, e.g., WO 2012/003348 A2, WO 2012/048040, US 2010/0256518 A1, WO 2012/036697 A1, WO 2011/103041 A1, and WO 2011/005720, all of which are incorporated herein by reference in their entireties.

Figure 4:
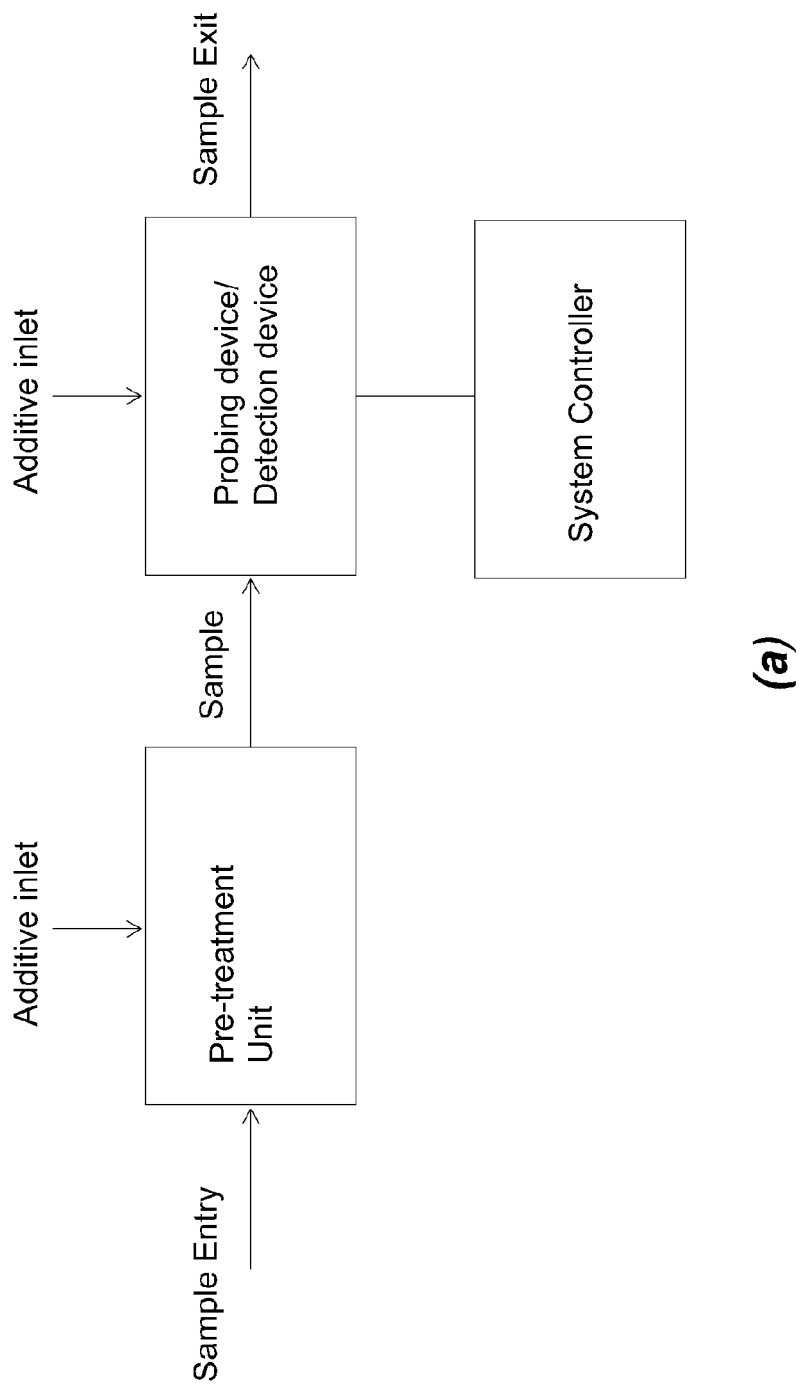
FIG. 4 shows the diagram of another apparatus of this invention for detecting disease and how additives enhance the measurement of microscopic property of the biological material.
Figure 4:
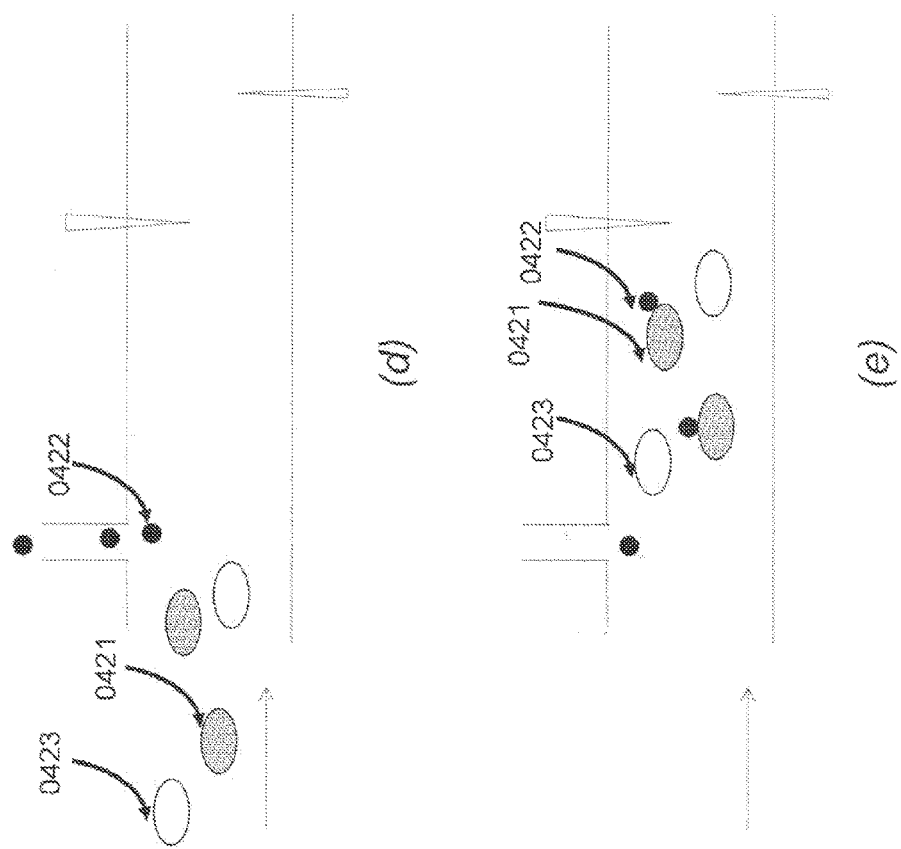

FIG. 4(*a*) illustrates a micro-device of this invention which includes at least a sample entry, a sample exit, an additive inlet, a pre-treat unit, a probing device, a detection device, and a system controller. In one embodiment, the additive inlet can be placed at the beginning of the process flow. For example, it can be located at the beginning portion of the pre-treatment unit. In another arrangement, multiple additive inlets can be placed at multiple locations in a machine, including at both pre-treatment unit and detection unit.

As illustrated in FIG. 4 (*b*), an additive 0422 can be introduced into the detection unit via additive inlet. The purpose of additive 0422 is to enhance measurement signal and therefore measurement sensitivity of biological subject 0421. In one embodiment, the additive 0422 has a higher measurement signal than that of biological subject 0421. In another embodiment, as shown in FIG. 4 (*c*), the additive 0422 can react with biological subject 0421 to form an aggregate, which has a higher measurement signal.

FIGS. 4(*d*) and 4(*e*) show yet another embodiment in which the additive 0422 can preferentially react with and/or absorb onto one type or types of biological subjects (biological subject 0422 in this case), thereby selectively enhancing signal from that type or types of biological subjects. For example, due to one or multiple characteristics of the said biological subject and/or additive (such as chemistry, surface properties such as chemistry and/or physical properties), the additive can react with or adsorb more strongly with one type or types of biological subjects than others. Thereby selectively enhancing measurement sensitivity of one type or types of biological subjects. One example would be a desired additive react with or adsorb more strongly with cancer cells and as a result, an enhanced or differentiated measurement signal is achieved.

The current invention is also aimed to resolve the issues encountered in the existing detection technologies and achieve the goals to carry out early stage cancer screening while still enabling identification of specific type of cancer such as bladder cancer, breast cancer, colon and rectal cancer, endometrial cancer, kidney cancer, leukemia cancer, lung cancer (including bronchus), melanoma cancer, non-Hodgkin lymphoma, pancreatic cancer, prostate cancer, thyroid cancer, with a high degree of sensitivity and specificity.

One of the keys to this innovation in meeting the above stated goals is a novel set of detection target additives, which are novel, nonobvious, and clearly differentiated from the traditional bio-markers in terms of their specific compositions, functions, and performance. Unlike the traditional bio-markers which are typically only sensitive to one type of detection target or cancer (or even a sub-type of a cancer such as lung cancer) for each bio-marker, such detection target additives can be used in general, early stage cancer screening with the ability to determine if there is cancer and what the specific type(s) of cancer. In terms of their compositions, the additives used in the present invention differ from the traditional bio-marker in that they contain a set of nonobvious, novel, and more diversified groups of bio-chemical, chemical, biological, and bio-physical components. In terms of their functions, unlike traditional bio-markers which often suffer from low specificity (thus a high degree of false count) and lack of ability to probe multiple cancer types (hence not suited for general purpose cancer screening and early stage cancer screening), the additives used in the present invention enable one to probe cancer with a high degree of both sensitivity and specificity, as well as to detect multiple cancer types with differentiated signals. Further, the detection methods of this invention, by utilizing the additives, can be used in conjunction with multiple components with multiple reaction paths comprising additives, samples to be detected, bio-chemicals (glucose, pyruvic acids, bromopyruvic acid, phosphoenolpyruvate (PEP), pyruvate kinase, pyruvate carboxylase, PEP carboxykinase, alanine, adenosine triphosphate, acetyl-coenzyme, oxaloacetate, lactate, ethanol, acetaldehyde, and fatty acids), chemicals (ions, catalysts, oxidizers, acidic acid, acetic acid, citric acid, tartaric acid, carcinogen, and organic components), biological components (proteins, enzymes, virus, cells, mitochondria, and power cells), and polymers. With the additives' novel and diversified composition groups, various mechanisms and reactions including a single reaction path or multiple reaction paths can be employed to probe cancer and its type, which include but are not limited to chemical reactions (oxidation reaction, reduction reaction, exothermal reaction, and catalytic reaction), surface chemical reaction, surface bio-chemical reaction, surface physical reaction, surface physical-chemical reaction, and surface bio-physical reaction, surface adsorption and surface absorption, biochemical reaction, and bio-physical reaction. In terms of performance, the methods of this invention are superior to the traditional methods and have overcome most of the bio-marker's limitations, which include their inability to achieve simultaneous sensitivity and specificity, inability to detect multiple cancer types (using a given bio-marker) and hence inability to be used in general purpose cancer screening, false diagnosis (when sensitivity is high), and relatively complex process.

In contrast to traditional bio-marker of pure biological nature, the novel detection target additives used for the methods of this invention include chemical, bio-chemical, and biological components, including but not limited to ions (e.g., $Fe^{3+}$, $Fe^{2+}$, $Ag^+$, $Cu^{2+}$, $Cr^{3+}$, $Na^+$, $K^+$, $Pt^{2+}$, $Mg^{2+}$, $H^+$, $Ca^{2+}$, $Hg^{2+}$, $Al^{3+}$, $NH_4^+$, $H_3O^+$, $Hg_2^{4+}$, $Cl^-$, $F^-$, $Br^-$, $O^{2-}$, $CO_3^{2-}$, $HCO_3^-$, $OH^-$, $NO_3^-$, $PO_4^{3-}$, $SO_4^{2-}$, $CH_3COO^-$, $HCOO^-$, $C_2O_4^{2-}$, and $CN^-$), oxidizers (e.g., $O_2$, $O_3$, $H_2O_2$, other inorganic oxides, $F_2$, $Cl_2$, $HNO_3$, nitrate compounds including ferric nitrate and silver nitrate, $H_2SO_4$, $H_2SO_5$, $H_2SO_8$, other persulfuric acids, chlorite, chlorate, perchlorate, other analogous halogen compounds, hypochlorite, other hypohalite compounds, NaClO, Hexavalent chromium compounds, permanganate compounds, sodium perborate, nitrous oxide, silver oxide, osmium retroxide, Tollen's reagents, 2,2'-dipyridyldisulfide (DPS), and bleach), catalysts, NaOH, KOH, $CO_2$, and CO. The role of the additives used in the methods of this invention is to probe biological entity to be measured to determine (a) if there is cancer in the sample and (b) what type of cancer in the sample, obtaining both measurement sensitivity for early stage cancer detection and specificity (to non-cancer components as well as specific cancers). Since the additives used in the methods of this invention are not purely biological in nature, it avoids the major issues encountered in typical bio-marker approaches. Instead, it can both probe low level cancer signals for general purpose cancer screening, as well as diagnosing which type of cancer through sensitive differentiation between different types of cancers (comparing detected signals with stored signatures for various types of cancers).

In one embodiment, the disclosed detection target additives can enhance the measurement sensitivity of the cancer detection parameters. In other embodiment, the additives used in the methods of this invention can be applied in conjunction of bio-marker(s). In yet another embodiment, the additives used in the methods of this invention can be utilized with at least one oxidizer for cancer detection. In still another embodiment, the additives used in the methods of this invention can be added to the sample to be measured and mixed for thorough reaction, and the sample is next centrifuged to separate out biological entities with additives attached, and finally detection is carried out on separated samples. In a general application, the novel detection process disclosed in this application comprises an additive, an oxidizer, a sample to be tested, a bio-marker, a chemical component, a biological component, and a bio-chemical component.

One of the roles of some of the additives used in the methods of this invention is to selectively attach to cancer entities (such as a cancerous cell). Another role is to selectively attach to non-cancerous entities. Another role is to react (comprising chemically, biologically, electrically, physically, thermal, mechanically, surface chemically, surface biologically, surface physically, surface bio-chemically, bio-chemically, bio-thermally, bio-physically, bio-electrically, and electro-chemically) with the sample or certain component(s) of the sample to be tested. Yet, another important role of such additives used in the methods of this invention is to probe the oxygen level at a microscopic level of a biological entity to be detected through reaction with the biological entity (such as cell or protein). Such reaction can be in electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical, and catalytic in nature. In addition to the above, in a general sense, the role of additives used in the methods of this invention is to interact and probe the biological entity being tested to extract information (such information including electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical), and enhance measurement sensitivity as well as specificity (to differentiate between normal entity and diseased entity, as well as between different cancer types).

In one embodiment, the additives used in the methods of this invention is to attach to cancer cells, while different type of cancerous cells attract different level of additives to the type of the cancer, which enables the identification of the types or sub-types of the cancer, by observing and classifying additives' level attached to a cancer cell, and further confirm the developing stage or period of a cancer by the quantity or concentration of the cancerous cells.

In another embodiment, reaction between the additives used in the methods of this invention and the biological entity can go through multiple paths, including but not limited to simple chemical reaction, simple biological reaction, simple bio-chemical reaction, oxidation, reduction. It also can include catalytic reaction, complex biological reactions and bio-chemical reactions. In still another embodiment, the additives used in the methods of this invention can react first with another component or components (for example, a bio-marker, an ion, an oxidizer, a protein, or a catalyst) in the detection system (for example, in the detection equipment and detection chamber), and then the resultant species (from the initial reaction(s)) react or probe the biological entity being tested.

In one important embodiment, an additive used in the methods of this invention disclosed in this application (such as catalyst or ion) can react with biological entity such as cells to probe oxygen level in the biological entity to obtain macroscopic and microscopic information. The obtained oxygen level can be correlated to whether the biological entity is cancerous or not, since cancerous cell often has a lower oxygen level while normal cell has a higher oxygen level. In another embodiment, an ion and/or a catalyst can be used to interact with oxygen in the biological entity, triggering a response which can then be measured (for example, gas evolution, thermal change, and charge redistribution, etc.). With a catalytic reaction, the signal can often get enhanced even with a low level of catalyst. In still another embodiment, a desired additive used in the methods of this invention can react and preferentially adsorbed (or absorbed) on to a particular location in a biological entity (such as a cell), resulting in a differentiated signal (between cancerous entity and normal entity) when one or more parameters are measured on such biological entities. For example, when a Fe ion is selectively adsorbed (or absorbed) onto a biological entity (such as a cell), it will change its local electrical field and charge distribution. It may also preferentially react with certain component(s) in the biological entity and provide a differentiated signal. In other words, an additive used in the methods of this invention may react with and/or adsorb (or absorb) onto cancerous cell and normal cell differently, which will enhance cancer detection sensitivity and possibly specificity (target), and/or result in a differentiated signal.

As another example of cancer detection, the additives used in the methods of this invention are used to probe mitochondria respiration and oxygen level in the cell, including pyruvic acid in the biological entity since pyruvic acid is an important compound at biochemistry, and it is a key to metabolic pathways. When oxygen is insufficient, it (pyruvate) breaks down anaerobically, and energy is generated through non-oxidative breakdown of glucose, which leads to cancer. In healthy cells where oxygen level is sufficient, energy is generated from oxidative breakdown of pyruvate.

With an additive used in the methods of this invention, one can better probe microscopic properties of the biological entity and its specific signature(s), identifying its entity (for example, which type of cell and hence which type of cancer).

In one of the embodiments, the additives used in the methods of this invention are added to the sample to be detected with some degree of selective interaction (including but not limited to attachment to certain components of the biological entity, chemical interaction, biological interaction, or bio-chemical interaction) with at least a certain component of the biological entity. Next, an alternating force or field, including but not limited to acoustic wave, optical beam, thermal wave, electrical current, electro-magnetic wave, is applied to the biological entity to be detected. Its response under this alternating force or field is then recorded. Such recorded data contains information related to the biological component (such as cancer cell) targeted by the additives used in the methods of this invention.

Detection of oxygen level and the detection hardware, process, and additives for cancer and other disease detection is an important innovative feature of this invention. Since it is difficult to detect low level of oxygen at a microscopic level (at DNA, RNA, protein, molecular, and cell level), novel ideas have been conceived in this patent application, in which the oxygen level is directly and indirectly measured (and calculated) using at least one detection enhancer and one micro-device. An enhancer is added to the biological sample being measured and its response is then measured. The measured response can be thermal signals (for example, from exothermal reaction), physical, physical-chemical, biochemical (for example, bubble formation (from reaction between the added catalyst and the biological sample and its mixture), optical signal (for example, light emission, light scattering due to bubble formation, color change due to oxygen level change), chain chemical reaction due to catalytic reaction between the additive (for example, enzyme, catalyst), chemical reaction, and electrical signals (current, voltage, surface charge, permeability of ions through membrane).

In one embodiment, an oxidizer is added first to the biological sample to be tested which reacts with the sample. A second additive which could be an enzyme or a catalyst is then added next. The added enzyme or catalyst can react with the oxidized biological sample (or the sample with raised oxygen level). Various properties can next be measured using the detectors in the micro-device.

In another embodiment, a biological component such as a protein is added first, which attach preferentially to certain site(s) of one or multiple types of biological species being tested. A second additive, which is easy to be tracked and/or at least one of whose properties can be easily measured, is added to the above mentioned mixture. The solution containing the first and second additives and the biological sample to be tested is measured in the micro-device using its detection probes. Optionally, the first and the second additives are mixed first and then added to the solution containing the biological sample. Optionally, the species with the first and the second additive attached can be separated from the rest of the solution using various separation methods, and then measured.

It is another important innovative feature to use enzyme and catalyst in conjunction with micro-device (and optionally with micro-devices' geometry-dependent factors (e.g., size, shape, and material including coating material), and measure one ore more properties and status of a biological sample to be tested (its optical, thermal, acoustical, chemical, physical, bio-chemical, bio-physical, mechanical, electrical, electro-magnetic properties, it size, surface area, hardness, elasticity, viscosity, and its flow speed) after the use of an enzyme or catalyst triggers a reaction or even a chain reaction (chemical, biological, and bio-chemical reactions) for enhanced response signals, which not only differentiate normal biological samples from diseased (for example, cancerous samples), but also obtain information on what type of disease (for example, what type of cancer). Sometimes it can be a one-step reaction, but it can also be a two-step or even three-step reaction.

In one embodiment, since enzymes are highly selective to substrates (for example, cell surface), the right type of enzyme selective to a given type of cancer can be used to screen that type of cancer, in conjunction of the micro-device disclosed in this application to achieve a degree of sensitivity and specificity. In another embodiment, multiple enzymes which are selective to multiple types of cancers can be used for general screening. If a patient from the above test is suspected to have a cancer, enzyme can be screened one by one to determine the type of cancer. The micro-device can be designed with multiple chambers (each chamber comprising at least one inlet for introducing at least an enzyme, a probing unit, and a detection unit) connected with one or more channels, with a biological sample being tested flowing through the chambers. As an illustration, a detection scheme using enzyme is shown below (in which the generated detection signal is detected by the micro-device, and it involves a catalytic reaction):

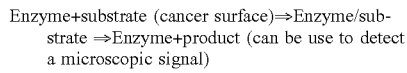

Enzyme+substrate (cancer surface)⇒Enzyme/substrate ⇒Enzyme+product (can be use to detect a microscopic signal)

This present invention is particularly useful for its ability to detect disease and even differentiate different types of diseases (for example, different types of cancers). Examples of different cancer cells include carcinoma, sarcoma, leukemia, lymphoma, and glioma. Those different types of cancer cells have differences in various properties including but not limited to physical, chemical, bio-chemical, bio-physical, mechanical, thermal, optical, electrical, magnetic, and electro-magnetic properties. For example, even within the carcinoma type of cancers, squamous cells are flat on the surface, while the adenomatous type of cancers are generally bulky (thus having a lower surface area to volume ratio than the squamous type cancers). Therefore, a group of enhancers which are easily absorbs or adsorbs on the surface of cancer can be employed in conjunction with the micro-devices for achieving improved measurement specificity for squamous type of cancers, while the same group of enhancers will have lower signal strength on adenomatous type of cancers.

Another difference would be in the cell surface and cell membrane properties of different types of cancers which more specifically will have different surface properties, oxygen level, oxygen bonding within the cell and cell surface, and various permeability and transport properties. As a result, by employing enhancers which can probe oxygen level and/or bonding site, permeability properties, transport properties, and surface properties of the biological samples such as cell, protein, DNA, RNA, and tissue.

In one embodiment, an enhancer containing an ion additive (e.g., Fe, Au, Ag, Cu, K, Ca, Na, and Cr) and good surface adsorption and absorption ability is utilized, which is mixed with a biological sample to be tested. The solution with the enhancer and biological sample is next tested in a micro-device of this invention.

In another embodiment, an enhancer containing at least one oxidizer (such as $H_2O_2$) is first mixed with the biological sample to be tested. The mixed solution is then tested in the micro-device.

In yet another embodiment, an enhancer containing at least one oxidizer (such as $H_2O_2$) is first mixed with the biological sample to be tested. A second enhancer containing at least one catalyst is added to the above solution next. The mixed solution is then tested in the micro-device.

Sometimes, one or more additives used in the methods of this invention (or other components such as an ion, a catalyst, an oxidizer, a protein, a chemical compound, a bio-chemical compound, or a polymer) can undergo multiple reactions, and adsorptions or absorptions before attaching or reacting to biological entities being detected.

A micro-device suitable for the methods of this invention can include multiple stages of probing or detection each provides a probing signal and detects a property at the microscopic level that can be the same as or different from the probing signal and detected property of another stage.

A multi-staged detecting device collects data in each stage and then normalizes and integrates the collected data to plot a characteristic curve to identify and diagnose the sample tested, for example, for diagnosis of the type of cancer. Specifically, among other things, at each stage, the device has a different geometry. In one embodiment, the difference in geometry of the device is the channel width and height (therefore, its cross-section). In another embodiment, the difference is in its length. In yet another embodiment, the difference is in its shape (for example, its cross-section can be circular, square, rectangular, oval and octagon). This geometrical factor, coupled with an applied probe (e.g., an optical beam, a thermal wave, a force, an acoustical wave, an electric voltage, an electronic current, or an electro-magnetic wave), and a measured response from the biological sample being measured provides information on the characteristics (a finger print) of a disease type. In one application, it provides information on the type of cancer. This geometrical factor along its properties of the biological sample being measured plays an important role in identifying the type(s) of cancer(s) in the sample. In another embodiment, the geometrical factor of the detection device, coupled with an applied probe (e.g., an optical beam, a thermal wave, a force, an acoustical wave, an electric voltage, an electronic current, or an electro-magnetic wave), at least one enhancer (including but not limited to an oxidizer, a catalyst, an enzyme, a reducing agent, an inhibitor, chemical component, a biological component, and a bio-chemical component), and a measured response from the biological sample being measured provides information on the characteristics (a finger print) of a disease type (e.g., the type of cancer). In yet another embodiment, the geometrical factor of the detection device, coupled with at least one enhancer (including but not limited to an oxidizer, a catalyst, an enzyme, a reducing agent, an inhibitor, chemical component, a biological component, and a bio-chemical component), and a measured response from the biological sample being measured provides information on the characteristics (a finger print) of a disease type (e.g., the type of cancer). In still another embodiment, the geometrical factor of the detection device, coupled with a measured response from the biological sample being measured provides information on the characteristics (a finger print) of a disease type (e.g., the type of cancer).

Figure 5:
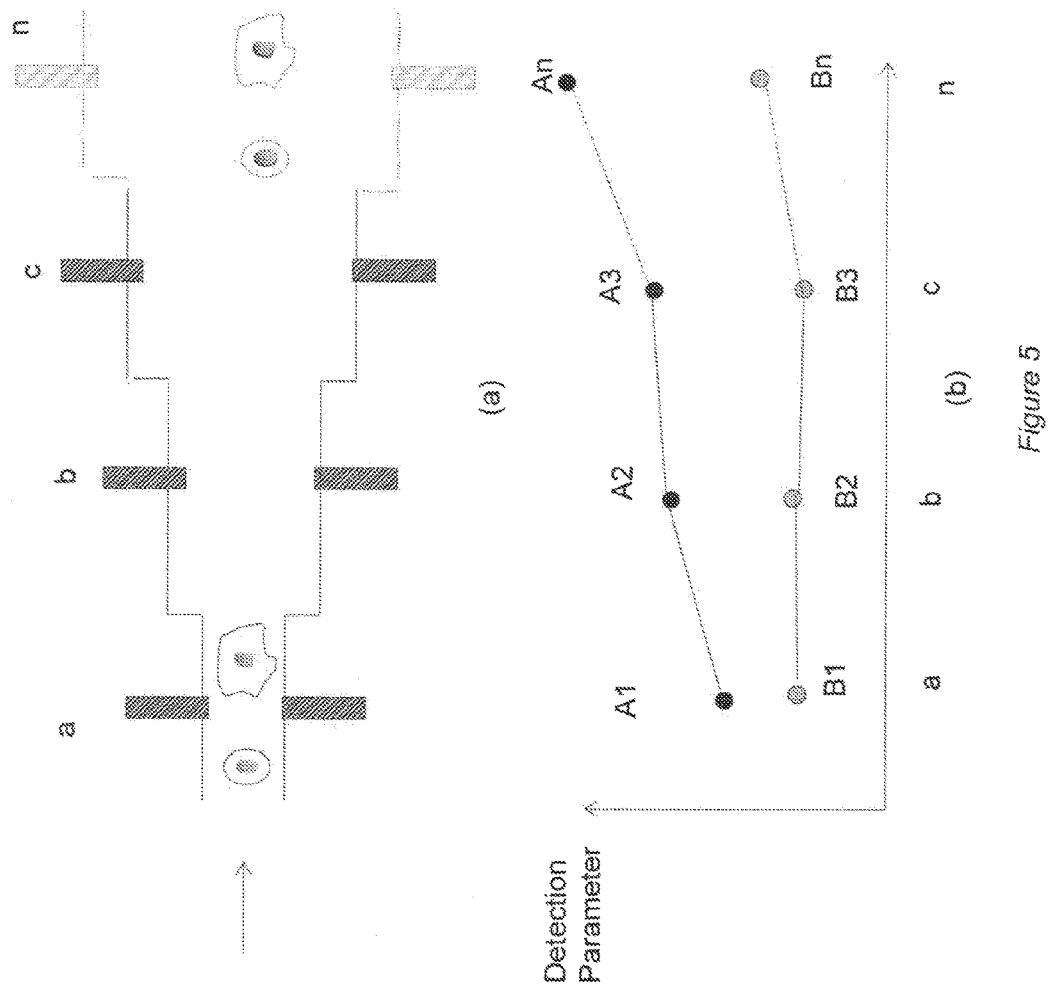
FIG. 5 illustrates how the method of this invention which uses bio-identifiers improves the sensitivity and specificity of the detection of disease.
Figure 5:
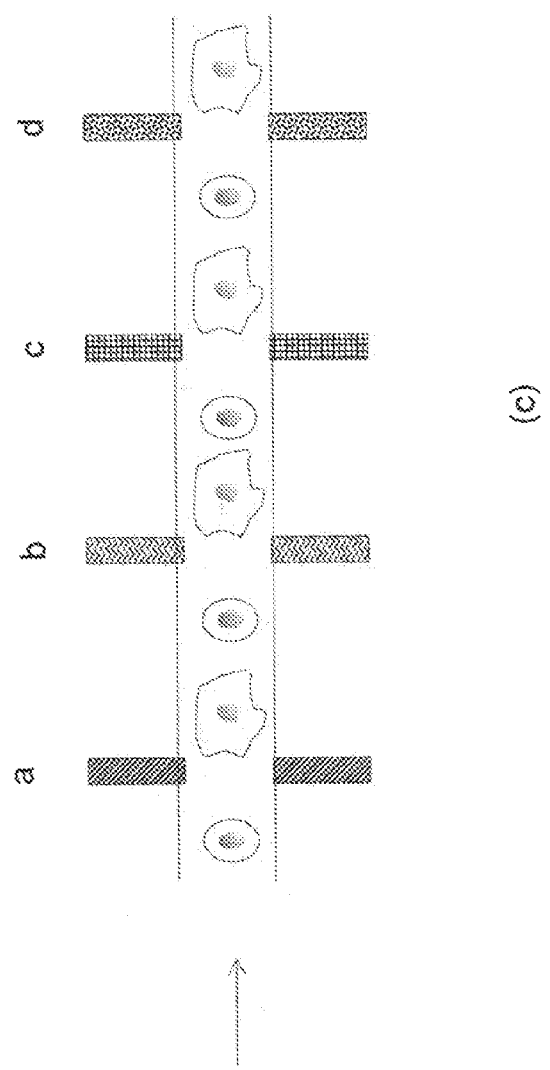
Figure 5:
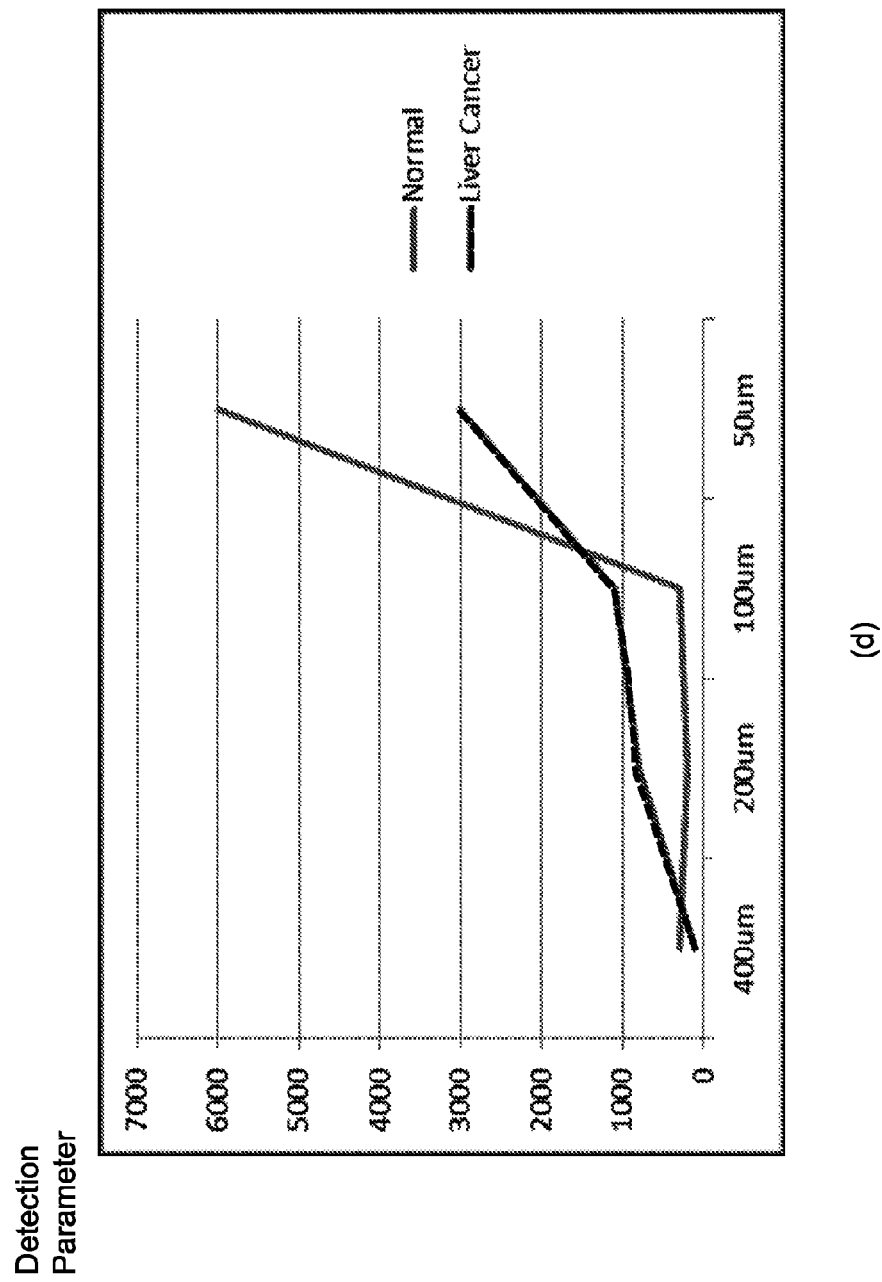
Figure 5:
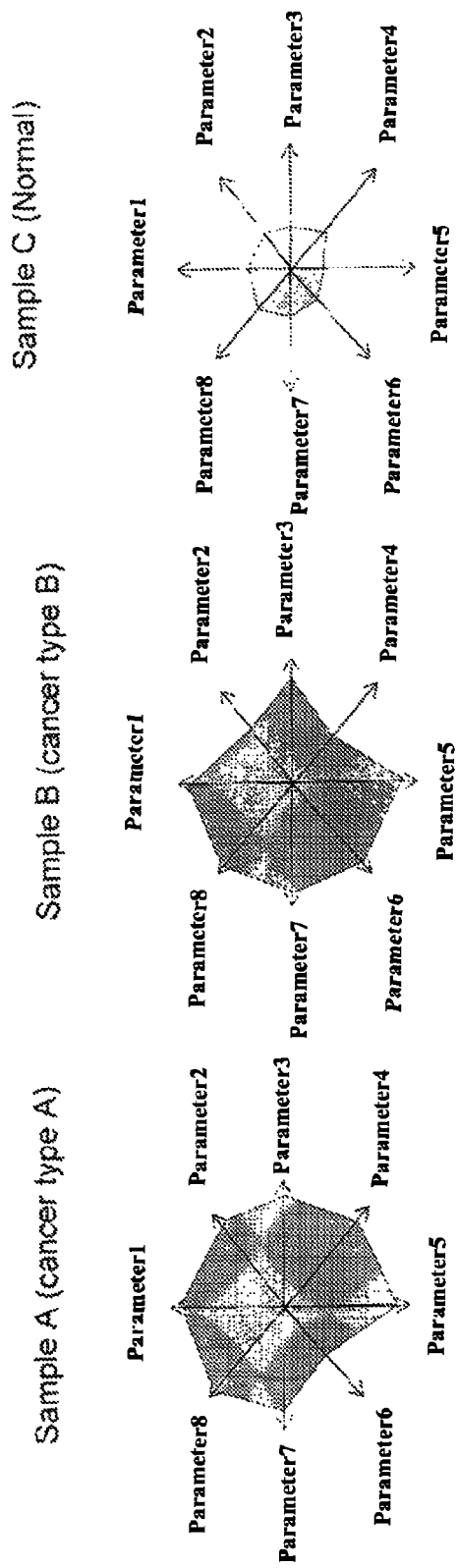

FIG. 5(a) depicts an embodiment of such devices with four different probing stages, identified as a, b, c, and n. These different stages differ from each other by the geometry of the channel—in this case the width of the channel in which the biological sample travels. In this embodiment, a biological entity is probed in all four stages and a same property is detected in each stage. The detection measurements or reading of the same property collected from the four stages can be used to plot a specific characteristic curve. See FIG. 5(b). The figure can then be used to identify the types of the tested biological sample (e.g., diseased cells) with comparison to the standing control group (e.g., non-diseased or healthy cells). In FIG. 5(b), A and B are different biological samples and result in different curves.

FIG. 5(c) illustrates another embodiment of the micro-device with multiple stages each different from the other by the probing units. The width and height of the channel in the different stages is the same. In this embodiment, two different biological samples are being probed and then detected. The measurements of the detected property can be normalized to plot a specific characteristic curve. FIG. 5(d) shows two different curves for the two different biological samples.

Multiple microscopic properties that are probed and then detected by various probing and detection units can composite a complex index, which is represented by the area inside the curves as well as the feature or shapes of the curves as shown in FIG. 5(e). This is more reliable than using a single microscopic property to determine the existence or type of disease (e.g., cancer or tumor). As shown in FIG. 5(c), cancer types A and B have different areas with regard to the standard control sample, while cancer type A and cancer type B have different features in shape as well as different contours. This provides better differentiation and identification between different types of cancers. This method allows for a multi-dimensional characterization of the tumor, and it is more sensitive and comprehensive than the traditional detection methods. Compared with traditional detection method which often only relies on one parameter or one approach for cancer detection, the method disclosed in this application which utilizes multiple parameters even including diverse properties (biological, bio-chemical, physical, bio-physical, chemical, mechanical, thermal, optical, electrical, electro-optical properties, etc.) provides much more reliable, complete, overall, accurate and sensitive information on the detection, and also improves detection specificity.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims All publications referenced herein are incorporated by reference in their entireties.

What is claimed is:

1. A method for detecting cancer in a biological subject, comprising the steps of:
    adding an additive to a sample of the biological subject's tissue or organ containing cancer cells and normal cells to provide a difference in a microscopic property between the cancer cells and normal cells;
    contacting the additive-containing sample with a microdevice capable of differentiating normal cells from cancer cells;
    separating the cancer cells and normal cells in the sample; and
    measuring a biological expression level or concentration of the cancer cells;
    wherein the additive comprises an oxidant, a reductant, an inhibitor, a catalyst, an enzyme, a bio-marker, a chemical-marker, a bio-chemical marker, a bio-active compound, a chemical component, a bio-chemical component, a biological component, an organic component, a metal-organic component, a bio-chemical component, an optical component, a florescence component, a protein, a virus, a coloring agent, an antibody, or a combination thereof;
    wherein the oxidant comprises oxygen, ozone, hydrogen peroxide, an inorganic peroxide, nitric acid, a nitrate compound, a chromium compound, a permanganate compound, sulfuric acid, persulfuric acid, fluorine, chlorine, bromine, iodine, chlorite, chlorate, perchlorate, a halogen compound, hyperchlorite, a hypohalite compound, sodium perborate, nitrous oxide, sliver oxide, osmium tetroxide, Tollens' reagent, 2,2'-dipyridyldisulfide, urea, silver nitrate, ferric nitrate, urea nitrogen, blood urea nitrogen, potassium permanganate, or a combination thereof;
    wherein the reductant comprises nascent hydrogen, a compound containing $Fe^{2+}$ ion, sodium amalgam, sodium borohydride, a sulfite compound, hydrazine, a compound containing the $Sn^{2+}$ ion, zinc-mercury amalgam, lithium aluminum hydride, Lindlar catalyst, formic acid, oxalic acid, ascorbic acid, a phosphite, a hypophosphite, phosphorous acid, or a combination thereof;
    wherein the bio-active compound comprises glucose, fructose, pyruvate, galactose, amino acid, acetic acid, glyoxylic acid, oxalic acid, propionic acid, or acetic acid; and
    wherein the halogen compound is 4-chlorotoluene, dibromopentane, bromoethane, 2-chloropropane, fluorocyclopentane, or 2-iodo-2-methylpentane; the hypohalite compound is hypoiodous acid, hypobromite, hypochlorite, or hypofluorous acid; the reductant compound containing $Fe^{2+}$ ion is iron(II) sulfate; the enzyme comprises an oxidoreductase, transferase, hydrolase, lyase, isomerase, ligase, RNA-enzyme, DNA polymerase, RNA polymerase, hexokinase, aminoacyl tRNA synthetase, ribosome, an artificial enzyme, or a cofactor-bound thereof.

2. The method of claim 1, further comprising adding one or more additional additives to the sample before the measuring step.

3. The method of claim 1, wherein the additive is added to the sample during the contacting step or the separating step.

4. The method of claim 1, wherein the reductase is dehydrogenase, luciferase, or DMSO reductase; and the hexokinase is pyruvate carboxylase or PEP carboxylinase.

5. The method of claim 2, where the additives can be the same or different.

6. The method of claim 1, wherein the step of separating the cancer cells and normal cells in the sample comprises subjecting the sample to one or more filters.

7. The method of claim 6, wherein the one or more filters differentiate the cancer cells and normal cells by their electrical, magnetic, electromagnetic, thermal, optical, acoustical, biological, chemical, electro-mechanical, electro-chemical, electro-optical, electro-thermal, electrochemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electromechanical-optical, bio-electro-thermal-optical, bio-electrochemical-mechanical, physical or mechanical property, or a combination thereof.

8. The method of claim 1, wherein the microscopic property is an electrical, magnetic, electromagnetic, thermal, optical, acoustical, biological, chemical, electro-mechanical, electro-chemical, electro-optical, electro-thermal, electrochemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electromechanical-optical, bio-electro-thermal-optical, bio-electrochemical-mechanical, physical or mechanical property, or a combination thereof.

9. The method of claim 8, wherein the electrical property is surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, speed of reaction, oxygen concentration, oxygen consumption rate, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, property relating to bio-markers, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, shear strength, elongation strength, fracture stress, adhesion, mechanical resonance frequency, elasticity, plasticity, or compressibility.

10. The method of claim 1, further comprising applying an external force or energy to the sample before the measuring step, and the application of the external force or energy results in enhanced difference of a microscopic property between the cancer cells and normal cells.

11. The method of claim 10, the external force or energy is a physical, chemical, biological, mechanical, thermal, optical, acoustical, electrical, magnetic, electromagnetic, electro-mechanical, electro-chemical, electro-chemical-mechanical, bio-chemical, bio-mechanical, bio-optical, bio-physical, bio-electro-mechanical, bio-electro-chemical, or bio-electro-chemical-mechanical, electro-optical, electro-chemical optical force or energy; the microscopic property is an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro chemical-mechanical, physical or mechanical property, or a combination thereof.

12. The method of claim 11, wherein the electrical property is surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, speed of reaction, oxygen concentration, oxygen consumption rate, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, property relating to bio-markers, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, shear strength, elongation strength, fracture stress, adhesion, mechanical resonance frequency, elasticity, plasticity, or compressibility.

13. The method of claim 1, wherein the method not only detects the existence of cancer in the biological subject but also differentiates between different types of cancer cells.

14. The method of claim 1, wherein the cancer is bladder cancer, breast cancer, colon cancer, rectal cancer, endometrial cancer, kidney cancer, leukemia cancer, lung cancer (including bronchus), melanoma cancer, non-Hodgkin lymphoma, pancreatic cancer, prostate cancer, or thyroid cancer.

15. The method of claim 13, wherein the differentiation of different types of cancer cells is based in part on the geometry of the micro-device, probing signal, change in the probing signal, or the biological sample.

16. The method of claim 13, wherein the differentiation of different types of cancer cells is based in part on cell surface properties, cell membrane properties, oxygen level, oxygen location, oxygen bonding, electric charge density, electric charge location, or dynamic properties of the electric charge of the biological sample.

17. The method of claim 16, wherein the cell surface or cell membrane properties comprise surface absorption and adsorption ability of the biological sample, the oxygen level, oxygen bonding on the cell surface or membrane, ion concentration, ion gradient, membrane resting potential, cell surface charge, the permeability and transportation ability of the membrane.

18. A method for detecting cancer in a biological subject, comprising the steps of:
   adding an additive to a sample of the biological subject's tissue or organ containing cancer cells and normal cells to provide a difference in a microscopic property between the cancer cells and normal cells;
   contacting the additive-containing sample with a micro-device capable of differentiating normal cells from cancer cells;
   separating the cancer cells and normal cells in the sample; and
   measuring a biological expression level or concentration of the cancer cells;
   wherein the additive comprises an oxidant, a reductant, an inhibitor, a catalyst, an enzyme, a bio-marker, a chemical-marker, a bio-chemical marker, a bio-active compound, a chemical component, a bio-chemical component, a biological component, an organic component, a metal-organic component, a bio-chemical component, an optical components, a florescence component, a protein, a virus, a coloring agent, an antibody, or a combination thereof;
   wherein the oxidant comprises oxygen, ozone, hydrogen peroxide, an inorganic peroxide, nitric acid, a nitrate compound, a chromium compound, a permanganate compound, sulfuric acid, persulfuric acid, fluorine, chlorine, bromine, iodine, chlorite, chlorate, perchlorate, a halogen compound, hyperchlorite, a hypohalite compound, sodium perborate, nitrous oxide, silver oxide, osmium tetroxide, Tollen's reagent, 2,2'-dipyridyldisulfide, urea, silver nitrate, ferric nitrate, urea nitrogen, blood urea nitrogen, potassium permanganate, or a combination thereof;
wherein the reductant comprises nascent hydrogen, a compound containing $Fe^{2+}$ ion, sodium amalgam, sodium borohydride, a sulfate compound, hydrazine, a compound containing the $Sn^{2+}$ ion, zinc-mercury amalgam, lithium aluminum hydride, Lindlar catalyst, formic acid, oxalic acid, ascorbic acid, a phosphite, a hypophosphite, phosphorous acid, or a combination thereof;
wherein the bio-active compound comprises glucose, fructose, pyruvate, galactose, amino acid, acetic acid, glyoxylic acid, oxalic acid, propionic acid or acetic acid; and further comprising the steps of:
before the additive adding step, placing the sample in a solvent to form a liquid phase sample solution;
before the additive adding step, introducing the additive to a nano-particle dispersion to form an additive dispersion; and
mixing the additive dispersion;
wherein the additive adding step comprises contacting the additive dispersion with the liquid phase sample solution.

19. A method for detecting cancer in a biological subject, comprising the steps of:
adding an additive to a sample of the biological subject's tissue or organ containing cancer cells and normal cells to provide a difference in a microscopic property between the cancer cells and normal cells;
contacting the additive-containing sample with a microdevice capable of differentiating normal cells from cancer cells;
separating the cancer cells and normal cells in the sample; and
measuring a biological expression level or concentration of the cancer cells;
wherein the additive comprises an oxidant, a reductant, an inhibitor, a catalyst, an enzyme, a bio-marker, a chemical-marker, a bio-chemical marker, a bio-active compound, a chemical component, a bio-chemical component, a biological component, an organic component, a metal-organic component, a bio-chemical component, an optical components, a florescence component, a protein, a virus, a coloring agent, an antibody, or a combination thereof;
wherein the oxidant comprises oxygen, ozone, hydrogen peroxide, an inorganic peroxide, nitric acid, a nitrate compound, a chromium compound, a permanganate compound, sulfuric acid, a halogen compound, hyperchlorite, a hypohalite compounds, sodium perborate, nitrous oxide, silver oxide, osmium tetroxide, Trollen's reagent, 2,2'-dipyridyldisulfide, urea, silver nitrate, ferric nitrate, urea nitrogen, blood urea nitrogen, potassium permanganate, or a combination thereof;
wherein the reductant comprises nascent hydrogen, a compound containing $Fe^{2+}$ ion, sodium amalgam, sodium borohydride, a sulfate compound, hydrazine, a compound containing the $Sn^{2+}$ ion, zinc-mercury amalgam, lithium aluminum hydride, Lindlar catalyst, formic acid, oxalic acid, ascorbic acid, a phosphite, a hypophosphite, phosphorous acid, or a combination thereof;
wherein the bio-active compound comprises glucose, fructose, pyruvate, galactose, amino acid, acetic acid, glyoxylic acid, oxide acid, propionic acid or acetic acid; and further comprising the steps of:
before the additive adding step, placing the sample in a solvent to form a liquid phase sample solution; and
adding one or more additional additives to the sample before the measuring step;
wherein the additive adding step comprises adding an oxidizer additive to the liquid phase sample solution, and
wherein the one or more additional additives are further added after the additive adding step, the one or more additional additives being selected from the group consisting of a catalyst, a bio-chemical additive, an inhibitor, a bio-marker, a chemical, an enzyme, a reducing agent, and a combination thereof.

20. A method for detecting cancer in a biological subject, comprising the steps of:
adding an additive to a sample of the biological subject's tissue or organ containing cancer cells and normal cells to provide a difference in a microscopic property between the cancer cells and normal cells;
contacting the additive-containing sample with a microdevice capable of differentiating normal cells from cancer cells;
separating the cancer cells and normal cells in the sample; and
measuring a biological expression level or concentration of the cancer cells;
wherein the additive comprises an oxidant, a reductant, an inhibitor, a catalyst, an enzyme, a bio-marker, a chemical-marker, a bio-chemical marker, a bio-active compound, a chemical component, a bio-chemical component, a biological component, an organic component, a metal-organic component, a bio-chemical component, an optical components, a florescence component, a protein, a virus, a coloring agent, an antibody, or combination thereof;
wherein the oxidant comprises oxygen, ozone, hydrogen peroxide, an inorganic peroxide, nitric acid, a nitrate compound, a chromium compound, a permanganate compound, sulfuric acid, persulfuric acid, fluorine, chlorine, bromine, iodine, chlorite, chlorate, perchlorate, a halogen compound, hyperchlorite, a hypohalite compound, sodium perborate, nitrous oxide, silver oxide, osmium tetroxide, Tollen's reagent, 2,2'-dipyridyldisulfide, urea, silver nitrate, ferric nitrate, urea nitrogen, blood urea nitrogen, potassium permanganate, or a combination thereof;
wherein the reductant comprises nascent hydrogen, a compound containing $Fe^{2+}$ ion, sodium amalgam, sodium borohydride, a sulfite compound, hydrazine, a compound containing the $Sn^{2+}$ ion, zinc-mercury amalgam, lithium aluminum hydride, Lindlar catalyst, formic acid, oxalic acid, ascorbic acid, a phosphite, a hypophosphite, phosphorous acid, or a combination thereof;
wherein the bio-active compound comprises glucose, fructose, pyruvate, galactose, amino acid, acetic acid, glyoxylic acid, oxalic acid, propionic acid or acetic acid; and further comprising the steps of:
before the additive adding step, placing the sample in a solvent to form a liquid phase sample solution; and
adding one or more additional additives to the sample before the measuring step;
wherein the additive adding step comprises adding a catalyst additive to the liquid phase sample solution; and wherein the one or more additional additives are further added after the additive adding step, the one or more additional additives being selected from the group consisting of an oxidizer, a bio-chemical additive, an inhibitor, a bio-marker, a chemical, an enzyme, a reducing agent, and a combination thereof.

21. A method for detecting cancer in a biological subject, comprising the steps of:
adding an additive to a sample of the biological subject's tissue or organ containing cancer cells and normal cells to provide a difference in a microscopic property between the cancer cells and normal cells;
contacting the additive-containing sample with a microdevice capable of differentiating normal cells from cancer cells;
separating the cancer cells and normal cells in the sample; and
measuring a biological expression level or concentration of the cancer cells;
wherein the additive comprises an oxidant, a reductant, an inhibitor, a catalyst, an enzyme, a bio-marker, a chemical-marker, a bio-chemical marker, a bio-active compound, a chemical component, a bio-chemical component, a biological component, an organic component, a metal-organic component, a bio-chemical component, an optical components, a florescence component, a protein, a virus, a coloring agent, an antibody, or a combination thereof;
wherein the oxidant comprises oxygen, ozone, hydrogen, peroxide, an inorganic peroxide, nitric acid, a nitrate compound, a chromium compound, a permanganate compound, sulfuric acid, persulfuric acid, fluorine, chlorine, bromine, iodine, chlorite, chlorate, perchlorate, a halogen compound, hyperchlorite, a hypohalite compound, sodium perborate, nitrous oxide, silver oxide, osmium tetroxide, Tollens'reagent, 2,2'-dipyridyldisulfide, urea, silver nitrate, ferric nitrate, urea nitrogen, blood urea nitrogen, potassium permanganate, or a combination thereof;
wherein the reductant comprises nascent hydrogen, a compound containing $Fe^{2+}$ ion, sodium amalgam, sodium borohydride, a sulfite compound, hydrazine, a compound containing the $Sn^{2+}$ ion, zinc-mercury amalgam, lithium aluminum hydride, Lindlar catalyst, formic acid, oxalic acid, ascorbic acid, a phosphite, a hypophosphite, phosphorous acid, or a combination thereof;
wherein the bio-active compound comprises glucose, fructose, pyruvate, galactose, amino acid, acetic acid, glypoxylic acid, oxalic acid, propionic acid or acetic acid; and further comprising the steps of:
before the additive adding step, placing the sample in a solvent to form a liquid phase sample solution; and
adding one or more additional additives to the sample before the measuring step:
wherein the additive adding step comprises adding a bio-chemical additive to the liquid phase sample solution, and
wherein the one or more additional additives are further added after the additive adding step, the one or more additional additives being selected from the group consisting of an oxidizer, a catalyst, an inhibitor, a bio-marker, a chemical, an enzyme, a reducing agent, and a combination thereof.

22. A method for detecting cancer in a biological subject, comprising the steps of:
adding an additive to a sample of the biological subject's tissue or organ containing cancer cells and normal cells to provide a difference in a microscopic property between the cancer cells and normal cells;
contacting the additive-containing sample with a microdevice capable of differentiating normal cells from cancer cells;
separating the cancer cells and the normal cells in the sample; and
measuring a biological expression level or concentration of the cancer cells;
wherein the additive comprises an oxidant, a reductant, an inhibitor, a catalyst, an enzyme, a bio-marker, a chemical-marker, a bio-chemical marker, a bio-active compound, a chemical component, a bio-chemical component, a biological component, an organic component, a metal-organic component, a bio-chemical component, an optical components, a florescence component, a protein, a virus, a coloring agent, an antibody, or combination thereof;
wherein the oxidant comprises oxygen, ozone, hydrogen peroxide, an inorganic peroxide, nitric acid, a nitrate compound, a chromium compound, a permanganate compound, sulfuric acid, persulfuric acid, fluorine, chlorine, bromine, iodine, chlorite, chlorate, perchlorate, a halogen compound, hyperchlorite, a hypohalite compound, sodium perborate, nitrous oxide, silver oxide, osmium tetroxide, Tollen's reagent, 2,2'-dipyridyldisulfide, urea, silver nitrate, ferric nitrate, urea nitrogen, blood urea nitrogen, potassium permanganate, or a combination thereof;
wherein the reductant comprises nascent hydrogen, a compound containing $Fe^{2+}$ ion, sodium amalgam, sodium borohydride, a sulfate compound, hydrazine, a compound containing the $Sn^{2+}$ ion, zinc-mercury amalgam, lithium aluminum hydride, Lindlar catalyst, formic acid, oxalic acid, ascorbic acid, a phosphite, a hypophosphite, phosphorous acid, or a combination thereof;
wherein the bio-active compound comprises glucose, fructose, pyruvate, galactose, amino acid, acetic acid, glyoxylic acid, oxalic acid, propionic acid or acetic acid; and further comprising the steps of:
before the additive adding step, placing the sample in a solvent to form a liquid phase sample solution; and
adding one or more additional additives to the sample before the measuring step:
wherein the additive adding step comprises adding a reducing agent additive to the liquid phase sample solution, and
wherein the one or more additional additives are further added after the additive adding step, the one or more additional additives being selected from the group consisting of an oxidizer, a catalyst, a bio-chemical additive, an inhibitor, a bio-marker, a chemical, an enzyme, and a combination thereof.

* * * * *